United States Patent
Prassler et al.

(10) Patent No.: US 9,062,097 B2
(45) Date of Patent: Jun. 23, 2015

(54) METHODS FOR THE FORMATION OF DISULPHIDE BONDS

(75) Inventors: Josef Prassler, Germering (DE); Yvonne Stark, Munich (DE)

(73) Assignee: Morpho Sys AG, Martinsried (DE)

( * ) Notice: Subject to any disclaimer, the term of this patent is extended or adjusted under 35 U.S.C. 154(b) by 546 days.

(21) Appl. No.: 12/664,533

(22) PCT Filed: Aug. 21, 2008

(86) PCT No.: PCT/EP2008/060931
§ 371 (c)(1),
(2), (4) Date: Dec. 14, 2009

(87) PCT Pub. No.: WO2009/024593
PCT Pub. Date: Feb. 26, 2009

(65) Prior Publication Data
US 2010/0190234 A1    Jul. 29, 2010

Related U.S. Application Data

(60) Provisional application No. 60/957,027, filed on Aug. 21, 2007, provisional application No. 60/989,035, filed on Nov. 19, 2007.

(51) Int. Cl.
  *C40B 50/06*  (2006.01)
  *C07K 19/00*  (2006.01)
  *C07K 16/00*  (2006.01)
  *C12N 15/10*  (2006.01)

(52) U.S. Cl.
  CPC .............. *C07K 19/00* (2013.01); *C40B 50/06* (2013.01); *C07K 16/005* (2013.01); *C07K 2317/55* (2013.01); *C12N 15/1037* (2013.01)

(58) Field of Classification Search
None
See application file for complete search history.

(56) References Cited

U.S. PATENT DOCUMENTS

| | | |
|---|---|---|
| 5,427,908 A | 6/1995 | Dower |
| 5,514,548 A | 5/1996 | Krebber |
| 5,698,424 A | 12/1997 | Mastico |
| 5,747,334 A | 5/1998 | Kay |
| 5,770,434 A | 6/1998 | Huse |
| 5,821,333 A | 10/1998 | Carter |
| 5,844,089 A * | 12/1998 | Hoffman et al. ............... 530/385 |

(Continued)

FOREIGN PATENT DOCUMENTS

| | | |
|---|---|---|
| WO | 8806630 | 9/1988 |
| WO | 9002809 | 3/1990 |

(Continued)

OTHER PUBLICATIONS

Kondo A et al: "Yeast cell-surface display—applications of molecular display" Applied Microbiology and Biotechnology, Springer Verlag, Berlin, DE, vol. 64, No. 1, Mar. 1, 2004, pp. 28-40, XP002296295 ISSN: 0175-7598.

(Continued)

*Primary Examiner* — Christian Boesen
(74) *Attorney, Agent, or Firm* — Paul F. Wiegel

(57) ABSTRACT

The present invention relates to methods for the formation of inter-molecular disulphide bonds, including (poly)peptides/proteins, nucleic acids, vectors, host cells and bacteriophages used in these methods. Furthermore the invention relates to the use of this method for the improved display of (poly)peptides/proteins on the surface of bacteriophage particles.

13 Claims, 11 Drawing Sheets

A typical CysDisplay vector

(56) References Cited

U.S. PATENT DOCUMENTS

| | | | |
|---|---|---|---|
| 5,866,344 A * | 2/1999 | Georgiou | 435/7.21 |
| 5,871,974 A | 2/1999 | Huse | |
| 5,945,311 A | 8/1999 | Lindhofer | |
| 6,017,732 A | 1/2000 | Jespers | |
| 6,309,642 B1 | 10/2001 | Cutler | |
| 6,341,256 B1 | 1/2002 | Deem | |
| 6,515,110 B1 | 2/2003 | Whitlow | |
| 6,962,702 B2 | 11/2005 | Hansen | |
| 7,049,135 B2 | 5/2006 | Rudert | |
| 7,052,872 B1 | 5/2006 | Hansen | |
| 7,083,784 B2 | 8/2006 | DallAcqua | |
| 7,183,076 B2 | 2/2007 | Arathoon | |
| 7,276,585 B2 | 10/2007 | Lazar | |
| 7,429,380 B2 | 9/2008 | Hori | |
| 7,566,695 B2 * | 7/2009 | Dasseux et al. | 514/1.1 |
| 2002/0034733 A1 * | 3/2002 | Lohning | 435/5 |
| 2004/0142430 A1 | 7/2004 | Hori | |
| 2005/0008649 A1 | 1/2005 | Shin | |
| 2005/0059082 A1 | 3/2005 | Breitling | |
| 2006/0204493 A1 | 9/2006 | Huang | |
| 2009/0163379 A1 | 6/2009 | Wang | |
| 2009/0226421 A1 | 9/2009 | Parren | |

FOREIGN PATENT DOCUMENTS

| | | |
|---|---|---|
| WO | 9117271 | 11/1991 |
| WO | 9119818 | 12/1991 |
| WO | 9201047 | 1/1992 |
| WO | 9209690 | 6/1992 |
| WO | 9400588 | 1/1994 |
| WO | 9708186 | 3/1997 |
| WO | 9740141 | 10/1997 |
| WO | 9936569 | 7/1999 |
| WO | 9958655 | 11/1999 |
| WO | 0105950 | 1/2001 |
| WO | 03012069 | 2/2003 |
| WO | 03029456 | 4/2003 |
| WO | 03060065 | 7/2003 |
| WO | 2004013276 | 2/2004 |
| WO | 2005063817 | 7/2005 |
| WO | 2005100590 | 10/2005 |
| WO | 2007048037 | 4/2007 |
| WO | 2007130520 | 11/2007 |
| WO | 2009024593 | 2/2009 |
| WO | 2009050237 | 4/2009 |
| WO | 2009050656 | 4/2009 |
| WO | 2009087230 | 7/2009 |

OTHER PUBLICATIONS

Pu W "Dimerization of leucine zippers analyzed by random selection" Department Biological Chemistry and Molecular Pharmacology, Harvard Medical School, Boston, 1993.
Kipriyanov et al., "Recombinant Single-chain Fv Fragments Carrying C-terminal Cysteine"; 1994; Molecular Immun.; vol. 31, No. 14, pp. 1047-1058.
Healy "Peptide Ligands for Integrin a& Selected from Random Phage Display Libraries" (Mar. 1995) Biochemistry vol. 34 pp. 3948 to 3955.
Barbas "Synthetic Human Antibodies: Selecting and Evolving Functional Proteins" (Oct. 1995) Methods vol. 8 pp. 94 to 103.
Koiwa (May 1998); Koiwa (May 1998) The Plant Journal vol. 14 pp. 371 to 379; The Plant Journal vol. 14 pp. 371 to 379.
Hattori, et al.: "Grafting of material-binding function into antibodies Functionalization by peptide grafting"; Biochemical and Biophysical Research Communications 365 (2008) 751-757, Nov. 2007.
Bortoletto Nicola et al: 'Optimizing anti-CD3 affinity for effective T cell targeting against tumor cells' European Journal of Immunology, Weinheim, DE, vol. 32, No. 11, Nov. 2002, pp. 3102-3107, XP002436763 ISSN: 0014-2980.
Muller K M et al: "A dimeric bispecific miniantibody combines two specificities with avidity" FEBS Letters, Elsevier, Amsterdam, NL, vol. 432, No. 1-2, Jul. 31, 1998, pp. 45-49, XP004259191 ISSN: 0014-5793.

Padiolleau-Lefevre et al: "Expression and detection strategies for an scFv fragment retaining the same high affinity than Fab and whole antibody: Implications for therapeutic use in prion diseases" Molecular Immunology, Elmsford, NY, US, vol. 44, No. 8, Dec. 1, 2006, pp. 1888-1896, XP005792725 ISSN: 0161-5890.
Ladner Robert C et al: 'Novel frameworks as a source of high-affinity ligands' Current Opinion in Biotechnology 2001, 12:406-410.
Lardner Biotechnology, vol. 12, No. 4, Aug. 2001, pp. 406-410, XP002524558 ISSN: 0958-1669.
Nuttall S D et al: "Design and Expression of Soluble CTLA-4 Variable Domain As a Scaffold for the Display of Functional Polypeptides" Proteins: Structure, Function and Genetics, John Wiley & Sons, Inc, US, vol. 36, No. 2, Jan. 1, 1999, pp. 217-227, XP000866035 ISSN: 0887-3585.
Goel A et al: "Relative position of the hexahistidine tag effects binding properties of a tumor-associated single-chain Fv construct" Biochimica Et Biophysica Acta—General Subjects, Elsevier Science Publishers, NL, vol. 1523, No. 1, Sep. 1, 2000, pp. 13-20, XP004276666 ISSN: 0304-4165.
Kahn, et al: 'Direct demonstration that receptor crosslinking or aggregation is important in insulin action' Proc. Natl. Acad. Sci. USA; vol. 75, No. 9, pp. 4209-4213, Sep. 1978; Biochemistry.
Mijares A. et al: 'From Agonist to Antagonist: Fab Fragments of an Agonist-Like Monoclonal Anti-b2-Adrenoceptor Antibody Behave as Antagonists'; Molecular Pharmacology; The American Society for Pharmacology and Experimental Therapeutics MOL 58:373-379, 2000 /203/842486.
Moroncini G. et al: 'Motif-grafted antibodies containing the replicative interface of cellular PrP are specific for PrPSc' 10404-10409, PNAS, Jul. 13, 2004, vol. 101, No. 28.
Frederickson S., et al: 'A rationally designed agonist antibody fragment that functionally mimics thrombopoietin', PNAS, Sep. 26, 2006, vol. 103, No. 39, 14307-14312.
Schneider H., et al: 'Homodimerization of Erythropoietin Receptor by a Bivalent Monoclonal Antibody Triggers Cell Proliferation and Differentiation of Erythroid Precursors'; Blood 1997 89: 473-482.
Schreiber A., et al: Biological Role of Epidermal Growth Factor-Receptor Clustering, Thej Ournalof Biolocicai. Chemistry, vol. 258, No. 2, Issue of danuary 25, pp. 846-853, 1982.
Wan Y, et al: "Epitope Map for a Growth Hormone Receptor Agonist Monoclonal Antibody, MAb 263", Mol. Endocrinol. 2003 17:2240-2250 originally published online Aug 7, 2003; doi: 10.1210/me. 2003-0162.
Todorovska Aneta, Design and application of diabodies, triabodies, and tetrabodies for cancer targeting, J. Immun. Meth. 248:47-66 (2001).
Plueckthun Andreas, New protein engineering approaches to multivalent and bispecific antibody fragments, Immunotechnology 3:83-105 (1997).
Kay "An M 13 phage library displaying random 3%amino-acid peptides as a source of novel sequences with affinity to selected targets" 1993 Gene 128(1), 59-65.
Tout & Lam Clinicaly and Dx Lab "Phage Display and Bacterial Expression of a Recombinant Fab Specific for *Pseudomonas aeruginosa* Serotype O6 Lipopolysaccharide" Immunol. 4(2): 147-155, 1997.
Albrecht, H., DeNardo, G.L. & DeNardo, S.J. (2006) Monospecific bivalent scFv-SH: Effects of linker length and location of an engineered cysteine on production, antigen binding activity and free Sh accessibility. Journal of Immunological Methods, 310, 100-116.
Bass, S., Greene, R. & Wells, J.A. (1990) Hormone phage: an enrichment method for variant proteins with altered binding properties. Proteins: Structure, Function and Genetics 8, 309-314.
Britto, P.J., Knipling, L. & Wolff, J. (2002) The Local Electrostatic Environment Determines Cysteine Reactivity in Tubulin. Journal of Biological Chemistry, 2002, 29018-29027.
Brinkmann et al. "Phage display of disulfide-stabilized Fv fragments", JIM 182 (1995) 41-50.
Bulja (Bulaj), G., Kortemme, T. & Goldenberg, D. P. (1998) Ionization-Reactivity Relationships for Cysteine Thiols in Polypeptides. Biochemistry 37, 8965-8972.
Crameri, R., & Suter, M. (1993). Display of biologically active proteins on the surface of filamentous phages: a cDNA cloning system

(56) References Cited

OTHER PUBLICATIONS for selection of functional gene products linked to the genetic information responsible for their production. Gene 137, 69-75.
Dunn, I. S. 1996. Phage display of proteins. Curr. Opin. Biotechnol. 7:547-553.
Gao, C., Mao, S., Lo, C.-H. L., Wirsching, P., Lerner, R. A., & Janda, K. D. (1999). Making artificial antibodies: A format for phage display of combinatorial heterodimeric arrays. Proc. Natl. Acad. Sci. U.S.A. 96, 6025-6030.
Greenwood J., Willis A.E. & Perham R.N. (1991) Multiple display of foreign peptides on a filamentous bacteriophage. Peptides from Plasmodium falciparum circumsporozoite protein as antigens. J. Mol. Biol. 220, 821-827.
Hansen, R.E:, Ostergaard, H. & Winther, J.R. (2005) Increasing the Reactivity of an Artificial Dithiol-Disulfide Pair through Modification of the Electrostatic Milieu. Biochemistry, 44, 5899-5906.
Hoogenboom "Selecting and screening recombinant antibody libraries" Nature Biotechnology, vol. 23, No. 9, Sep. 1, 2005 pp. 1105-1116.
Jespers L. S., Messens J. H., De Keyser A., Eeckhout D., Van d. B., I, Gansemans Y. G., Lauwereys M. J., Vlasuk G. P. & Stanssens P. E. (1995). Surface expression and ligand-based selection of cDNAs fused to filamentous phage gene Vi. Biotechnology (N.Y.) 13, 378-382.
Maruyama I. N., Maruyama H. I. & Brenner S. (1994) Lambda foo: a lambda phage vector for the expression of foreign proteins. Proc. Natl. Acad. Sci. U.S.A. 91, 8273-8277.
Matthias Paschke: "Phage Display systems and their applications" Applied Microbiology and Biotechnology, Springer, Berlin, vol. 70, No. 1, Mar. 1, 2006, pp. 2-11.
McGregor, D. (1996). Selection of proteins and peptides from libraries displayed on filamentous bacteriophage. Mol. Biotechnol. 6:155-162.
Mikawa Y. G., Maruyama I. N. & Brenner S. (1996). Surface display of proteins on bacteriophage lambda heads. J. Mol. Biol. 262, 21-30.
Parmley S. F. & Smith G.P. (1988) Antibody-selectable filamentous fd phage vectors: affinity purification of target genes. Gene 73, 305-318.
Singh R. et al. "Reductive unfolding and oxidative refolding of Bowman-birk inhibitor . . . " Biochimica Et Biophysica Acta, Elsevier Science BV, vol. 1597, No. 2, Jun. 3, 2002, pp. 280-291.
Smith G. P. (1985). Filamentous fusion phage: novel expression vectors that display cloned antigens on the virion surface. Science 228, 1315-1317.
Snyder, G.H., Cennerazzo, M.J., Karalis, a.J. & Filed, D. (1981). Electrostatic Influence of Local Cysteine Environments on Disulfide Exchange Kinetics. Biochemistry 20, 6509-6519.
Snyder, G.H., Reddy, M.K., Cennerazzo, M.J. & Filed, D. (1983).Use of local electrostatic environments of cysteines to enhance formation of a desired species in a reversible disulfide exchange reaction. Biochimica et Biophysica Acta 749, 219-226.
Sternberg N. & Hoess R. H. (1995). Display of peptides and proteins on the surface of bacteriophage lambda. Proc. Natl. Acad. Sci. U.S.A. 92, 1609-1613.
Yang et al: "Identification and characterization of the functional amino acids . . . " Journal of Biological Chemistry, vol. 266, No. 19, 1991, pp. 12759-12765.
Leichert et al. "Protein Thiol Modifications in Vivo" PLOS Biology, vol. 2, Issue 11, Nov. 2004, e333.
Griffiths et al. "The Reactivity and Oxidation Pathway of Cysteine 232 in Recombinant Human a1-Antitrypsin" Journal of Biochemical Chemistry, vol. 277, No. 28, pp. 25486-25492, 2002.
Georgiou et al. "How to Flip the (Redox) Switch" Cell, vol. 111, 607-610, Nov. 27, 2002.

\* cited by examiner

Figure 1: A typical CysDisplay vector
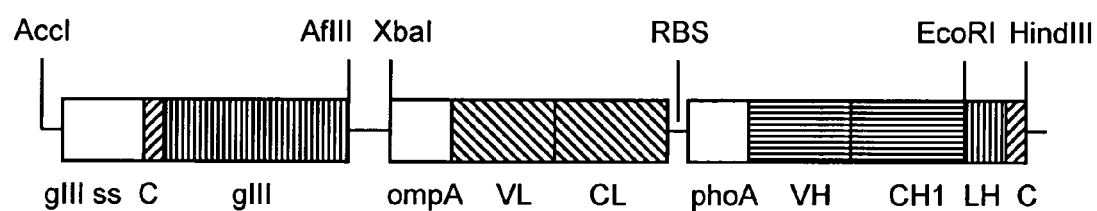

Figure 2: Binding to Ni-NTA plates
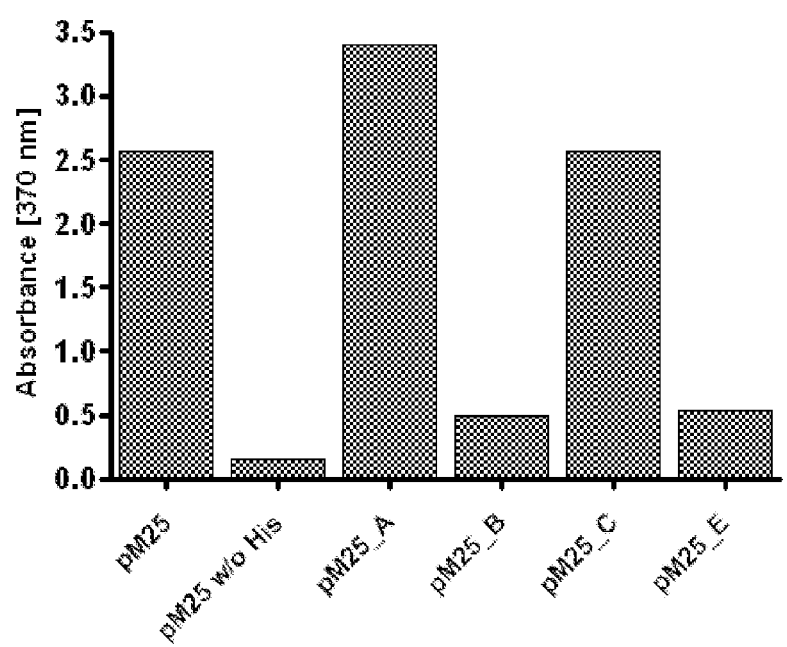

Figure 3: Functional display rates of pMORPH25 versions A, B and C
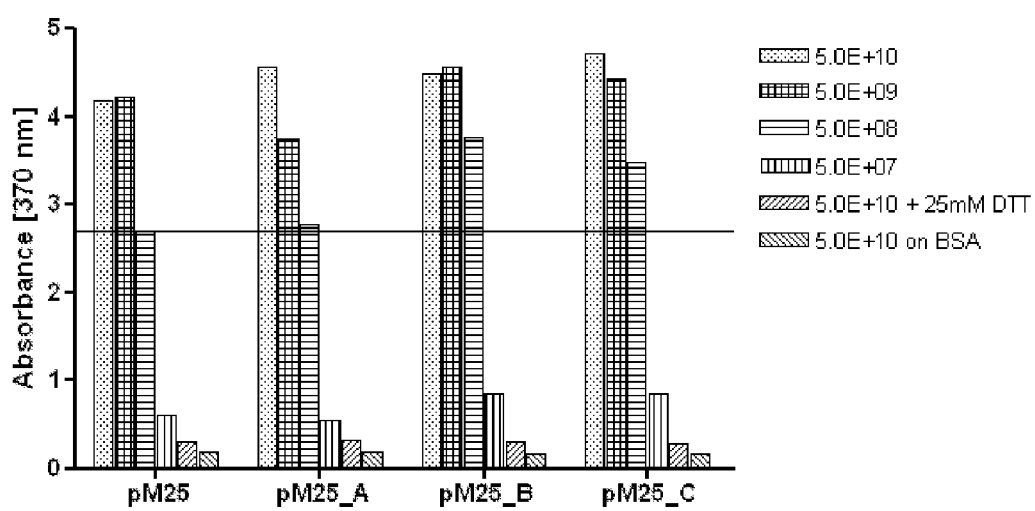

Figure 4: Functional display rate of pMORPH25 version E
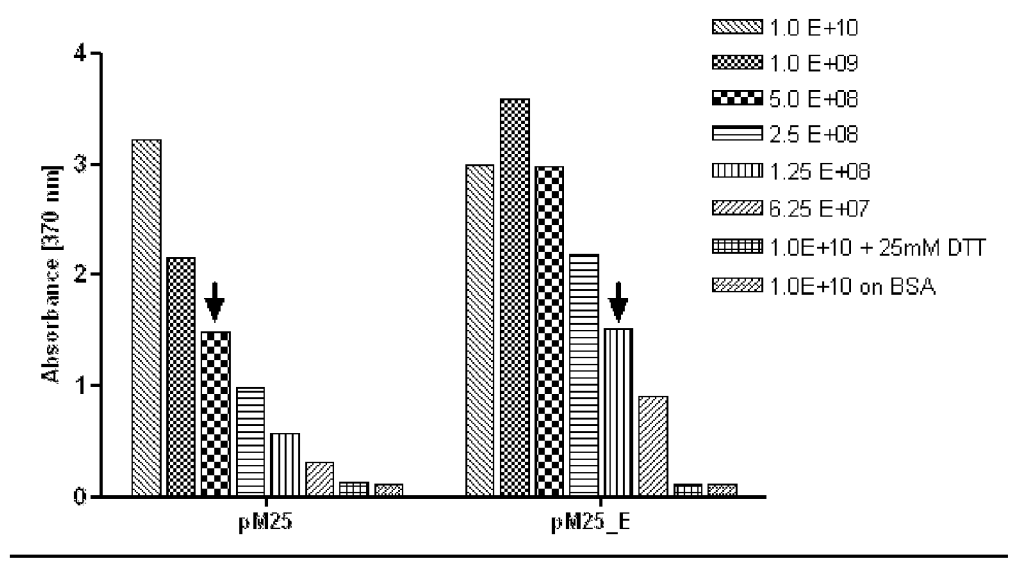

Figure 5 A: Sequence of a pMORPH23-derivative containing an Estrodiol-BSA specific HuCAL Fab fragment ctcgtatgttgtgtggaattgtgagcggataacaatttcacacaggaaacagctatgaccatgattacgaatttctagtatacgagg
gcaaaaaatgaaaaaactgctgttcgcgattccgctggtggtgccgttctatagccatagcgactactgcgacatcgagtttgca
gaaacagttgaaagttgtttagcaaaaccccatacagaaaattcatttactaacgtctggaaagacgacaaaactttagatcgtta
cgctaactatgagggctgtctgtggaatgctacaggcgttgtagtttgtactggtgacgaaactcagtgttacggtacatgggttcct
attgggcttgctatccctgaaaatgagggtggtggctctgagggtggcggttctgagggtggcggctctgagggtggcggtacta
aacctcctgagtacggtgatacacctattccgggctatacttatatcaaccctctcgacggcacttatccgcctggtactgagcaaa
accccgctaatcctaatccttctcttgaggagtctcagcctcttaatactttcatgtttcagaataataggttccgaaataggcagggg
gcattaactgtttatacgggcactgttactcaaggcactgaccccgttaaaacttattaccagtacactcctgtatcatcaaaagcc
atgtatgacgcttactggaacggtaaattcagagactgcgcttttccattctggctttaatgaggatccattcgtttgtgaatatcaagg
ccaatcgtctgacctgcctcaacctcctgtcaatgctggcggcggctctggtggtggttctggtggcggctctgagggtggcggct
ctgagggtggcggttctgagggtggcggctctgagggtggcggttccggtggcggctccggttccggtgattttgattatgaaaaa
atggcaaacgctaataagggggctatgaccgaaaatgccgatgaaaacgcgctacagtctgacgctaaaggcaaacttgatt
ctgtcgctactgattacggtgctgctatcgatggtttcattggtgacgtttccggccttgctaatggtaatggtgctactggtgattttgct
ggctctaattcccaaatggctcaagtcggtgacggtgataattcacctttaatgaataatttccgtcaatatttaccttctttgcctcagt
cggttgaatgtcgcccttatgtctttggcgctggtaaaccatatgaattttctattgattgtgacaaaataaacttattccgtggtgtcttt
gcgtttcttttatatgttgccaccttttatgtatgtattttcgacgtttgctaacatactgcgtaataaggagtcttaagtaatctagataacg
agggcaaaaaatgaaaaagacagctatcgcgattgcagtggcactggctggtttcgctaccgtagcgcaggccgatatcgtgc
tgacccagagcccggcgaccctgagcctgtctccgggcgaacgtgcgaccctgagctgcagagcgagccagtctgtttctcgtt
cttatctggcttggtaccagcagaaaccaggtcaagcaccgcgtctattaatttatggtgcttctcgtcgtgcaactggggtcccgg
cgcgttttagcggctctggatccggcacggattttaccctgaccattagcagcctggaacctgaagactttgcgacttattattgcca
gcagcgtggtaattattctattacctttggccagggtacgaaagttgaaattaaacgtacggtggctgctccgagcgtgtttattttcc
gccgagcgatgaacaactgaaaagcggcacggcgagcgtggtgtgcctgctgaacaacttttatccgcgtgaagcaaagtt
cagtggaaagtagacaacgcgctgcaaagcggcaacagccaggaaagcgtgaccgaacaggatagcaaagatagcacc
tattctctgagcagcaccctgaccctgagcaaagcggattatgaaaaacataaagtgtatgcgtgcgaagtgacccatcaaggt
ctgagcagcccggtgactaaatcttttaatcgtggcgaggcctgataagcatgcgtaggagaaaataaaatgaaacaaagcac
tattgcactggcactcttaccgttgctcttcacccctgttaccaaagcccaggtgcaattggtggaaagcggcggcggcctggtgc
aaccgggcggcagcctgcgtctgagctgcgcggcctccggatttaccttttcttcttatggtggtaattgggtgcgccaagcccctg
ggaagggtctcgagtgggtgagcggtatccattattctggtagctctacctattatgcggatagcgtgaaaggccgttttaccatttc
acgtgataattcgaaaaacaccctgtatctgcaaatgaacagcctgcgtgcggaagatacggccgtgtattattgcgcgcgtgct
cttcataagtgggctggttggggttttgatcattggggccaaggcaccctggtgacggttagctcagcgtcgaccaaaggtccaa
gcgtgtttccgctggctccgagcagcaaaagcaccagcggcggcacggctgccctgggctgcctggttaaagattatttcccgg
aaccagtcaccgtgagctggaacagcggggcgctgaccagcggcgtgcataccttccggcggtgctgcaaagcagcggcct
gtatagcctgagcagcgttgtgaccgtgccgagcagcagcttaggcactcagacctatatttgcaacgtgaaccataaaccgag

Figure 5 B caacaccaaagtggataaaaaagtggaaccgaaaagcgaattcccaggggggagcggaggcgcgccgcaccatcatcac
catcactgctgataagcttgacctgtgaagtgaaaaatggcgcagattgtgcgacattttttttgtctgccgtttaatgaaattgtaaa
cgttaatattttgttaaaattcgcgttaaattttgttaaatcagctcattttttaaccaataggccgaaatcggcaaaatcccttataaat
caaaagaatagaccgagatagggttgagtgttgttccagtttggaacaagagtccactattaaagaacgtggactccaacgtca
aagggcgaaaaaccgtctatcagggcgatggcccactacgagaaccatcaccctaatcaagttttttggggtcgaggtgccgta
aagcactaaatcggaaccctaaagggagcccccgatttagagcttgacggggaaagccggcgaacgtggcgagaaagga
agggaagaaagcgaaaggagcgggcgctagggcgctggcaagtgtagcggtcacgctgcgcgtaaccaccacacccgcc
gcgcttaatgcgccgctacagggcgcgtgctagccatgtgagcaaaaggccagcaaaaggccaggaaccgtaaaaaggcc
gcgttgctggcgttttccataggctccgcccccctgacgagcatcacaaaaatcgacgctcaagtcagaggtggcgaaacccg
acaggactataaagataccaggcgtttccccctggaagctccctcgtgcgctctcctgttccgaccctgccgcttaccggatacct
gtccgcctttctcccttcgggaagcgtggcgctttctcatagctcacgctgtaggtatctcagttcggtgtaggtcgttcgctccaagct
gggctgtgtgcacgaaccccccgttcagtccgaccgctgcgccttatccggtaactatcgtcttgagtccaacccggtaagacac
gacttatcgccactggcagcagccactggtaacaggattagcagagcgaggtatgtaggcggtgctacagagttcttgaagtgg
tggcctaactacggctacactagaagaacagtatttggtatctgcgctctgctgtagccagttaccttcggaaaaagagttggtag
ctcttgatccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcagatctagcacc
aggcgtttaagggcaccaataactgccttaaaaaaattacgccccgccctgccactcatcgcagtactgttgtaattcattaagca
ttctgccgacatggaagccatcacaaacgcatgatgaacctgaatcgccagcggcatcagcaccttgtcgccttgcgtataata
tttgcccatagtgaaaacgggggcgaagaagttgtccatattggctacgtttaaatcaaaactggtgaaactcacccagggattg
gctgagacgaaaaacatattctcaataaacccttlagggaaataggccaggttttcaccgtaacacgccacatcttgcgaatatat
gtgtagaaactgccggaaatcgtcgtggtattcactccagagcgatgaaaacgtttcagtttgctcatggaaaacggtgtaacaa
gggtgaacactatcccatatcaccagctcaccgtctttcattgccatacggaactccgggtgagcattcatcaggcgggcaagaa
tgtgaataaaggccggataaaacttgtgcttatttttctttacggtctttaaaaaggccgtaatatccagctgaacggtctggttatag
gtacattgagcaactgactgaaatgcctcaaaatgttctttacgatgccattgggatatatcaacggtggtatatccagtgatttttttct
ccattttagcttccttagctcctgaaaatctcgataactcaaaaaatacgcccggtagtgatcttatttcattatggtgaaagttggaa
cctcacccgacgtctaatgtgagttagctcactcattaggcaccccaggctttacactttatgcttccgg

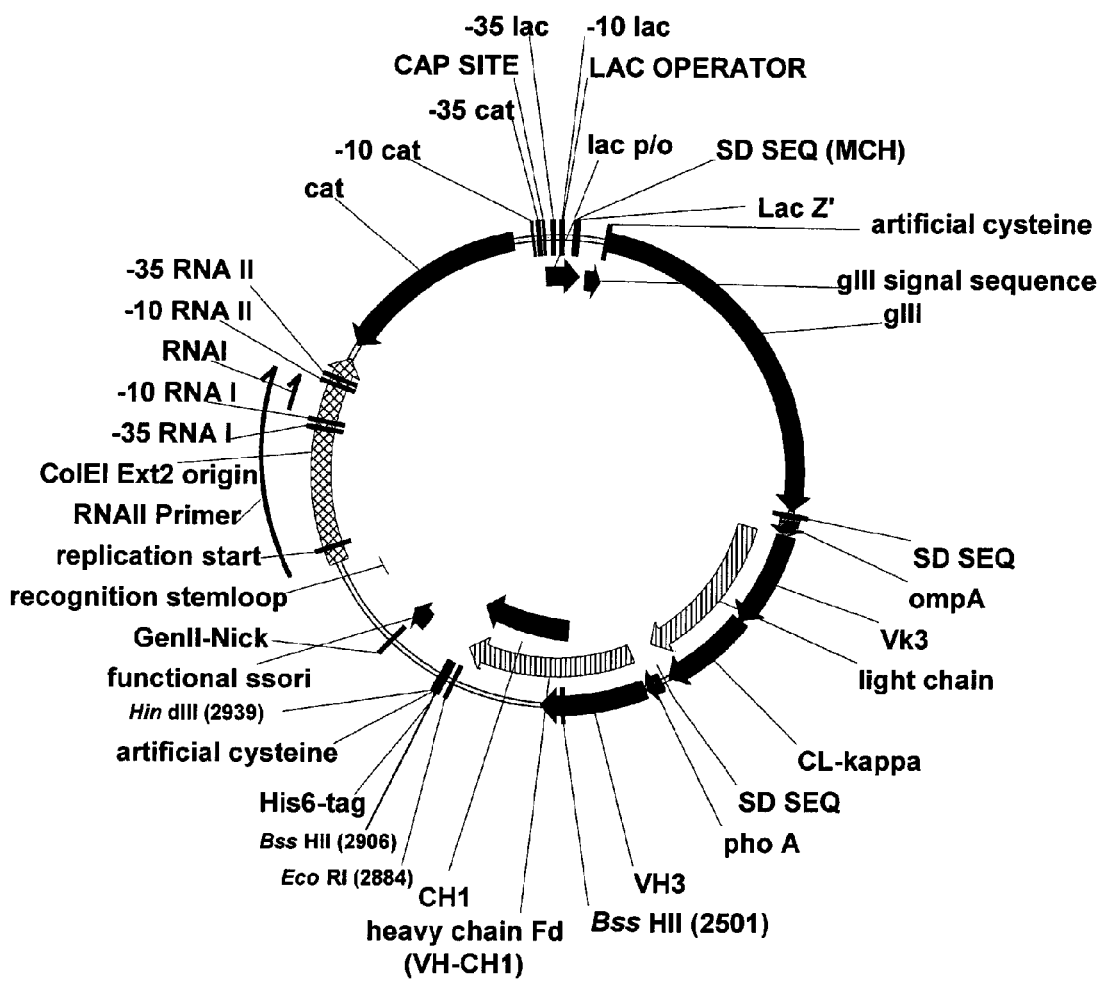
Figure 6: Vector map of a pMORPH23-derivative containing an Estrodiol-BSA specific HuCAL Fab fragment

Figure 7 A: Sequence of a pMORPH25- derivative containing an Estrodiol-BSA specific HuCAL Fab fragment ctcgtatgttgtgtggaattgtgagcggataacaatttcacacaggaaacagctatgaccatgattacgaatttctagtatacgagg
gcaaaaaatgaaaaaactgctgttcgcgattccgctggtggtgccgttctatagccatagcgactactgcgacatcgagtttgca
gaaacagttgaaagttgtttagcaaaacccatacagaaaattcatttactaacgtctggaaagacgacaaaactttagatcgtta
cgctaactatgagggctgtctgtggaatgctacaggcgttgtagtttgtactggtgacgaaactcagtgttacggtacatggttcct
attgggcttgctatccctgaaaatgagggtggtggctctgagggtggcggttctgagggtggcggctctgagggtggcggtacta
aacctcctgagtacggtgatacacctattccgggctatacttatatcaaccctctcgacggcacttatccgcctggtactgagcaaa
accccgctaatcctaatccttctcttgaggagtctcagcctcttaatactttcatgtttcagaataataggttccgaaataggcagggg
gcattaactgtttatacgggcactgttactcaaggcactgaccccgttaaaacttattaccagtacactcctgtatcatcaaaagcc
atgtatgacgcttactggaacggtaaattcagagactgcgctttccattctggctttaatgaggatccattcgtttgtgaatatcaagg
ccaatcgtctgacctgcctcaacctcctgtcaatgctggcggcggctctggtggtggttctggtggcggctctgagggtggcggct
ctgagggtggcggttctgagggtggcggctctgagggtggcggttccggtggcggctccggttccggtgattttgattatgaaaaa
atggcaaacgctaataagggggctatgaccgaaaatgccgatgaaaacgcgctacagtctgacgctaaaggcaaacttgatt
ctgtcgctactgattacggtgctgctatcgatggtttcattggtgacgtttccggccttgctaatggtaatggtgctactggtgattttgct
ggctctaattcccaaatggctcaagtcggtgacggtgataattcacctttaatgaataatttccgtcaatatttaccttctttgcctcagt
cggttgaatgtcgcccttatgtctttggcgctggtaaaccatatgaattttctattgattgtgacaaaataaacttattccgtggtgtcttt
gcgtttcttttatatgttgccacctttatgtatgtattttcgacgtttgctaacatactgcgtaataaggagtcttaagtaatctagataacg
agggcaaaaaatgaaaaagacagctatcgcgattgcagtggcactggctggtttcgctaccgtagcgcaggccgatatcgtgc
tgacccagagcccggcgaccctgagcctgtctccgggcgaacgtgcgaccctgagctgcagagcgagccagtctgtttctcgtt
cttatctggcttggtaccagcagaaaccaggtcaagcaccgcgtctattaatttatggtgcttctcgtcgtgcaactggggtcccgg
cgcgttttagcggctctggatccggcacggattttaccctgaccattagcagcctggaacctgaagactttgcgacttattattgcca
gcagcgtggtaattattctattacctttggccagggtacgaaagttgaaattaaacgtacggtggctgctccgagcgtgtttattttcc
gccgagcgatgaacaactgaaaagcggcacggcgagcgtggtgtgcctgctgaacaacttttatccgcgtgaagcgaaagtt
cagtggaaagtagacaacgcgctgcaaagcggcaacagccaggaaagcgtgaccgaacaggatagcaaagatagcacc
tattctctgagcagcaccctgaccctgagcaaagcggattatgaaaaacataaagtgtatgcgtgcgaagtgacccatcaaggt
ctgagcagcccggtgactaaatcttttaatcgtggcgaggcctgataagcatgcgtaggagaaaataaaatgaaacaaagcac
tattgcactggcactcttaccgttgctcttcacccctgttaccaaagcccaggtgcaattggtggaaagcggcggcggcctggtgc
aaccgggcggcagcctgcgtctgagctgcgcggcctccggatttaccttttcttcttatggtggtaattgggtgcgccaagcccctg
ggaagggtctcgagtgggtgagcggtatccattattctggtagctctacctattatgcggatagcgtgaaaggccgttttaccatttc
acgtgataattcgaaaaacaccctgtatctgcaaatgaacagcctgcgtgcggaagatacggccgtgtattattgcgcgcgtgct
cttcataagtgggctggttggggttttgatcattggggccaaggcaccctggtgacggttagctcagcgtcgaccaaaggtccaa
gcgtgtttccgctggctccgagcagcaaaagcaccagcggcggcacggctgccctgggctgcctggttaaagattatttcccgg
aaccagtcaccgtgagctggaacagcggggcgctgaccagcggcgtgcataccttccggcggtgctgcaaagcagcggcct
gtatagcctgagcagcgttgtgaccgtgccgagcagcagcttaggcactcagacctatatttgcaacgtgaaccataaaccgag
caacaccaaagtggataaaaaagtggaaccgaaaagcgaattcccagggggagcggaggtgcgccgcaccatcatcac

Figure 7 B:

catcactgctgataagcttgacctgtgaagtgaaaaatggcgcagattgtgcgacatttttttttgtctgccgtttaatgaaattgtaaa
cgttaatattttgttaaaattcgcgttaaattttttgttaaatcagctcattttttaaccaataggccgaaatcggcaaaatcccttataaat
caaaagaatagaccgagatagggttgagtgttgttccagtttggaacaagagtccactattaaagaacgtggactccaacgtca
aagggcgaaaaaccgtctatcagggcgatggcccactacgagaaccatcaccctaatcaagttttttggggtcgaggtgccgta
aagcactaaatcggaaccctaaagggagcccccgatttagagcttgacggggaaagccggcgaacgtggcgagaaagga
agggaagaaagcgaaaggagcgggcgctagggcgctggcaagtgtagcggtcacgctgcgcgtaaccaccacacccgcc
gcgcttaatgcgccgctacagggcgcgtgctagccatgtgagcaaaaggccagcaaaaggccaggaaccgtaaaaaggcc
gcgttgctggcgttttccataggctccgcccccctgacgagcatcacaaaaatcgacgctcaagtcagaggtggcgaaacccg
acaggactataaagataccaggcgtttccccctggaagctccctcgtgcgctctcctgttccgaccctgccgcttaccggatacct
gtccgcctttctcccttcgggaagcgtggcgctttctcatagctcacgctgtaggtatctcagttcggtgtaggtcgttcgctccaagct
gggctgtgtgcacgaaccccccgttcagtccgaccgctgcgccttatccggtaactatcgtcttgagtccaacccggtaagacac
gacttatcgccactggcagcagccactggtaacaggattagcagagcgaggtatgtaggcggtgctacagagttcttgaagtgg
tggcctaactacggctacactagaagaacagtatttggtatctgcgctctgctgtagccagttaccttcggaaaaagagttggtag
ctcttgatccggcaaacaaaccaccgctggtagcggtggtttttttgtttgcaagcagcagattacgcgcagaaaaaaaggatct
caagaagatcctttgatcttttctacggggtctgacgctcagtggaacgaaaactcacgttaagggattttggtcagatctagcacc
aggcgtttaagggcaccaataactgccttaaaaaaattacgccccgccctgccactcatcgcagtactgttgtaattcattaagca
ttctgccgacatggaagccatcacaaacggcatgatgaacctgaatcgccagcggcatcagcaccttgtcgccttgcgtataata
tttgcccatagtgaaaacgggggcgaagaagttgtccatattggctacgtttaaatcaaaactggtgaaactcacccagggattg
gctgagacgaaaaacatattctcaataaacccttagggaaataggccaggttttcaccgtaacacgccacatcttgcgaatatat
gtgtagaaactgccggaaatcgtcgtggtattcactccagagcgatgaaaacgtttcagtttgctcatggaaaacggtgtaacaa
gggtgaacactatcccatatcaccagctcaccgtctttcattgccatacggaactccgggtgagcattcatcaggcgggcaagaa
tgtgaataaaggccggataaaacttgtgcttattttttctttacggtctttaaaaaggccgtaatatccagctgaacggtctggttatag
gtacattgagcaactgactgaaatgcctcaaaatgttctttacgatgccattgggatatatcaacggtggtatatccagtgatttttttct
ccattttagcttccttagctcctgaaaatctcgataactcaaaaaatacgcccggtagtgatcttatttcattatggtgaaagttggaa
cctcacccgacgtctaatgtgagttagctcactcattaggcaccccaggctttacactttatgcttccgg

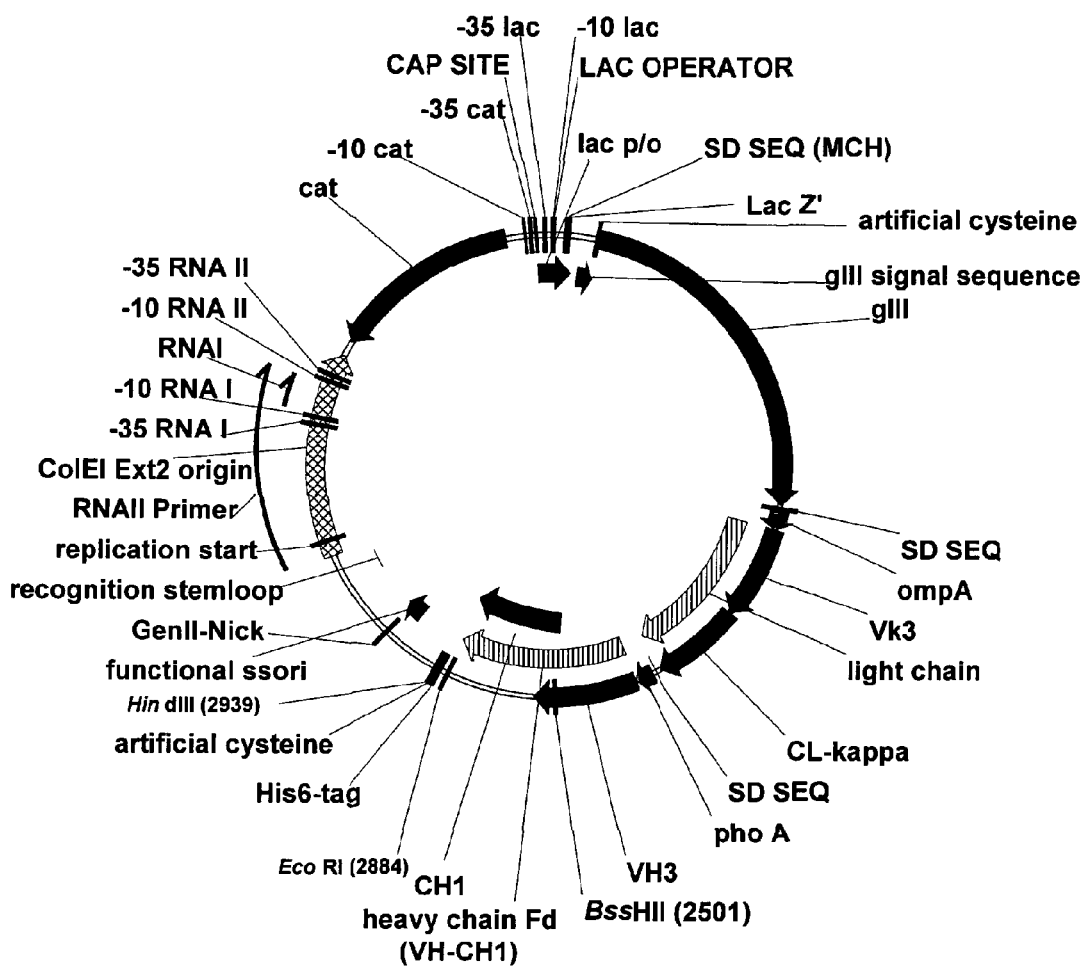
Figure 8: Vector map of a pMORPH25-derivative containing an Estrodiol-BSA specific HuCAL Fab fragment

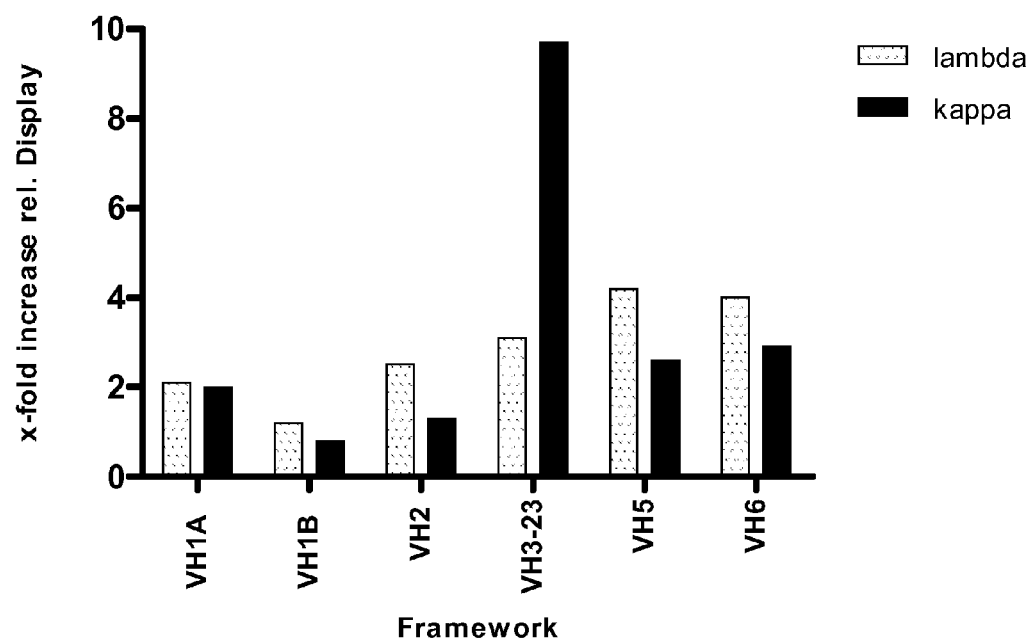
Figure 9: Relative display rate of different VH framework libraries of constructs of the present invention compared to the corresponding framework of conventional constructs.

SEQUENCE LISTING

```
<160> NUMBER OF SEQ ID NOS: 22

<210> SEQ ID NO 1
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aattcccagg ggggagcgga ggtgcgccgc accatcatca ccatcactgc aaatgata        58

<210> SEQ ID NO 2
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
agcttatcat ttgcagtgat ggtgatgatg gtgcggcgca cctccgctcc ccctggg        58

<210> SEQ ID NO 3
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aattcccagg ggggagcgga ggtgcgccgc accatcataa acatcactgc tgata        55

<210> SEQ ID NO 4
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
agcttatcag cagtgatgtt tatgatggtg cggcgcacct ccgctccccc ctggg        55

<210> SEQ ID NO 5
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
```

```
aattcccagg ggggagcgga ggtgcgccgc accatcatca ccataaatgc tgata          55
```

<210> SEQ ID NO 6
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6

```
agcttatcag catttatggt gatgatggtg cggcgcacct ccgctccccc ctggg          55
```

<210> SEQ ID NO 7
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7

```
aattcccagg ggggagcgga ggtgcgccgc acaaacataa acataaatgc tgata          55
```

<210> SEQ ID NO 8
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8

```
agcttatcag catttatgtt tatgtttgtg cggcgcacct ccgctccccc ctggg          55
```

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 9

```
His His His His His His
1               5
```

<210> SEQ ID NO 10
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

```
His His His Lys His His
1               5
```

<210> SEQ ID NO 11
<211> LENGTH: 6
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

His His His His His Lys
1               5

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

His Lys His Lys His Lys
1               5

<210> SEQ ID NO 13
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Pro Gly Gly Ser Gly Gly Ala Pro His His His His His Cys
1               5                   10                  15

<210> SEQ ID NO 14
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Pro Gly Gly Ser Gly Gly Ala Pro His His His His His Cys Lys
1               5                   10                  15

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Pro Gly Gly Ser Gly Gly Ala Pro His His Lys His His Cys
1               5                   10                  15

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
Synthetic peptide"

<400> SEQUENCE: 16

Pro Gly Gly Ser Gly Gly Ala Pro His His His His Lys Cys
1               5                   10                  15

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Pro Gly Gly Ser Gly Gly Ala Pro His Lys His Lys His Lys Cys
1               5                   10                  15

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 5xHis tag"

<400> SEQUENCE: 18

His His His His His
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

His Lys His Lys His Lys Cys
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

His His His His His His Cys
1               5

<210> SEQ ID NO 21
<211> LENGTH: 5049
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
```

```
ctcgtatgtt gtgtggaatt gtgagcggat aacaatttca cacaggaaac agctatgacc      60
atgattacga atttctagta tacgagggca aaaaatgaaa aaactgctgt tcgcgattcc     120
gctggtggtg ccgttctata gccatagcga ctactgcgac atcgagtttg cagaaacagt     180
tgaaagttgt ttagcaaaac cccatacaga aaattcattt actaacgtct ggaaagacga     240
caaaacttta gatcgttacg ctaactatga gggctgtctg tggaatgcta caggcgttgt     300
agtttgtact ggtgacgaaa ctcagtgtta cggtacatgg gttcctattg gcttgctat      360 ccctgaaaat gagggtggtg gctctgaggg tggcggttct gagggtggcg gctctgaggg     420
tggcggtact aaacctcctg agtacggtga tacacctatt ccgggctata cttatatcaa     480
ccctctcgac ggcacttatc cgcctggtac tgagcaaaac cccgctaatc ctaatccttc     540
tcttgaggag tctcagcctc ttaatacttt catgtttcag aataataggt tccgaaatag     600
gcagggggca ttaactgttt atacgggcac tgttactcaa ggcactgacc ccgttaaaac     660
ttattaccag tacactcctg tatcatcaaa agccatgtat gacgcttact ggaacggtaa     720
attcagagac tgcgctttcc attctggctt taatgaggat ccattcgttt gtgaatatca     780
aggccaatcg tctgacctgc ctcaacctcc tgtcaatgct ggcggcggct ctggtggtgg     840
ttctggtggc ggctctgagg gtggcggctc tgagggtggc ggttctgagg gtggcggctc     900
tgagggtggc ggttccggtg gcggctccgg ttccggtgat tttgattatg aaaaaatggc     960
aaacgctaat aaggggggcta tgaccgaaaa tgccgatgaa aacgcgctac agtctgacgc    1020
taaaggcaaa cttgattctg tcgctactga ttacggtgct gctatcgatg gtttcattgg    1080
tgacgtttcc ggccttgcta atggtaatgg tgctactggt gattttgctg gctctaattc    1140
ccaaatggct caagtcggtg acggtgataa ttcacctttα atgaataatt ccgtcaata    1200 tttaccttct ttgcctcagt cggttgaatg tcgcccttat gtctttggcg ctggtaaacc    1260
atatgaattt tctattgatt gtgacaaaat aaacttattc cgtggtgtct ttgcgtttct    1320
tttatatgtt gccaccttta tgtatgtatt ttcgacgttt gctaacatac tgcgtaataa    1380
ggagtcttaa gtaatctaga taacgagggc aaaaaatgaa aagacagct atcgcgattg    1440 cagtggcact ggctggtttc gctaccgtag cgcaggccga tatcgtgctg acccagagcc    1500
cggcgaccct gagcctgtct ccgggcgaac gtgcgaccct gagctgcaga gcgagccagt    1560
ctgtttctcg ttcttatctg gcttggtacc agcagaaacc aggtcaagca ccgcgtctat    1620
taatttatgg tgcttctcgt cgtgcaactg gggtcccggc gcgttttagc ggctctggat    1680
ccggcacgga ttttaccctg accattagca gcctggaacc tgaagacttt gcgacttatt    1740
attgccagca gcgtggtaat tattctatta cctttggcca gggtacgaaa gttgaaatta    1800
aacgtacggt ggctgctccg agcgtgttta ttttccgcc gagcgatgaa caactgaaaa    1860
gcggcacggc gagcgtggtg tgcctgctga caaacttta tccgcgtgaa gcgaaagttc    1920
agtggaaagt agacaacgcg ctgcaaagcg gcaacagcca ggaaagcgtg accgaacagg    1980
atagcaaaga tagcacctat tctctgagca gcaccctgac cctgagcaaa gcggattatg    2040
aaaaacataa agtgtatgcg tgcgaagtga cccatcaagg tctgagcagc ccggtgacta    2100 aatctttaa tcgtggcgag gcctgataag catgcgtagg agaaaataaa atgaaacaaa    2160
gcactattgc actggcactc ttaccgttgc tcttcacccc tgttaccaaa gcccaggtgc    2220
aattggtgga aagcggcggc ggcctggtgc aaccgggcgg cagcctgcgt ctgagctgcg    2280
cggcctccgg atttaccttt tcttcttatg gtggtaattg ggtgcgccaa gcccctggga    2340
agggtctcga gtgggtgagc ggtatccatt attctggtag ctctacctat tatgcggata    2400
```

-continued

```
gcgtgaaagg ccgttttacc atttcacgtg ataattcgaa aaacaccctg tatctgcaaa    2460
tgaacagcct gcgtgcggaa gatacggccg tgtattattg cgcgcgtgct cttcataagt    2520
gggctggttg gggttttgat cattggggcc aaggcaccct ggtgacggtt agctcagcgt    2580
cgaccaaagg tccaagcgtg tttccgctgg ctccgagcag caaaagcacc agcggcggca    2640
cggctgccct gggctgcctg gttaaagatt atttcccgga accagtcacc gtgagctgga    2700
acagcggggc gctgaccagc ggcgtgcata ccttccggc ggtgctgcaa agcagcggcc    2760
tgtatagcct gagcagcgtt gtgaccgtgc cgagcagcag cttaggcact cagacctata    2820
tttgcaacgt gaaccataaa ccgagcaaca ccaaagtgga taaaaagtg gaaccgaaaa    2880 gcgaattccc agggggagc ggaggcgcgc cgcaccatca tcaccatcac tgctgataag    2940
cttgacctgt gaagtgaaaa atggcgcaga ttgtgcgaca ttttttttgt ctgccgttta    3000
atgaaattgt aaacgttaat attttgttaa aattcgcgtt aaattttgt taaatcagct    3060 catttttaa ccataggcc gaaatcggca aaatccctta taaatcaaaa gaatagaccg    3120
agatagggtt gagtgttgtt ccagtttgga acaagagtcc actattaaag aacgtggact    3180
ccaacgtcaa agggcgaaaa accgtctatc agggcgatgg cccactacga gaaccatcac    3240
cctaatcaag ttttttgggg tcgaggtgcc gtaaagcact aaatcggaac cctaaaggga    3300 gccccgatt tagagcttga cggggaaagc cggcgaacgt ggcgagaaag gaagggaaga    3360
aagcgaaagg agcgggcgct agggcgctgg caagtgtagc ggtcacgctg cgcgtaacca    3420
ccacacccgc cgcgcttaat gcgccgctac agggcgcgtg ctagccatgt gagcaaaagg    3480
ccagcaaaag gccaggaacc gtaaaaaggc cgcgttgctg gcgttttcc ataggctccg    3540 cccccctgac gagcatcaca aaaatcgacg ctcaagtcag aggtggcgaa acccgacagg    3600
actataaaga taccaggcgt ttccccctgg aagctccctc gtgcgctctc ctgttccgac    3660
cctgccgctt accggatacc tgtccgcctt tctcccttcg ggaagcgtgg cgctttctca    3720
tagctcacgc tgtaggtatc tcagttcggt gtaggtcgtt cgctccaagc tgggctgtgt    3780
gcacgaaccc cccgttcagt ccgaccgctg cgccttatcc ggtaactatc gtcttgagtc    3840
caacccggta agacacgact tatcgccact ggcagcagcc actggtaaca ggattagcag    3900
agcgaggtat gtaggcggtg ctacagagtt cttgaagtgg tggcctaact acggctacac    3960
tagaagaaca gtatttggta tctgcgctct gctgtagcca gttaccttcg gaaaaagagt    4020
tggtagctct tgatccggca aacaaaccac cgctggtagc ggtggttttt tgtttgcaa    4080 gcagcagatt acgcgcagaa aaaaggatc tcaagaagat cctttgatct tttctacggg    4140
gtctgacgct cagtggaacg aaaactcacg ttaagggatt ttggtcagat ctagcaccag    4200
gcgtttaagg gcaccaataa ctgccttaaa aaaattacgc cccgccctgc cactcatcgc    4260
agtactgttg taattcatta agcattctgc cgacatggaa gccatcacaa acggcatgat    4320
gaacctgaat cgccagcggc atcagcacct tgtcgccttg cgtataatat ttgcccatag    4380
tgaaaacggg ggcgaagaag ttgtccatat tggctacgtt taaatcaaaa ctggtgaaac    4440
tcacccaggg attggctgag acgaaaaaca tattctcaat aaaccctta gggaaatagg    4500 ccaggttttc accgtaacac gccacatctt gcgaatatat gtgtagaaac tgccggaaat    4560
cgtcgtggta ttcactccag agcgatgaaa acgtttcagt ttgctcatgg aaaacggtgt    4620
aacaagggtg aacactatcc catatcacca gctcaccgtc tttcattgcc atacggaact    4680
ccgggtgagc attcatcagg cgggcaagaa tgtgaataaa ggccggataa aacttgtgct    4740
```

```
tattttttctt tacggtctttt aaaaaggccg taatatccag ctgaacggtc tggttatagg    4800
tacattgagc aactgactga aatgcctcaa aatgttcttt acgatgccat tgggatatat    4860
caacggtggt atatccagtg atttttttct ccattttagc ttccttagct cctgaaaatc    4920
tcgataactc aaaaaatacg cccggtagtg atcttatttc attatggtga aagttggaac    4980
ctcacccgac gtctaatgtg agttagctca ctcattaggc accccaggct ttacacttta    5040
tgcttccgg                                                              5049
```

<210> SEQ ID NO 22
<211> LENGTH: 5049
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
ctcgtatgtt gtgtggaatt gtgagcggat aacaatttca cacaggaaac agctatgacc      60
atgattacga atttctagta tacgagggca aaaaatgaaa aaactgctgt tcgcgattcc     120
gctggtggtg ccgttctata gccatagcga ctactgcgac atcgagtttg cagaaacagt     180
tgaaagttgt ttagcaaaac cccatacaga aaattcattt actaacgtct ggaaagacga     240
caaaacttta gatcgttacg ctaactatga gggctgtctg tggaatgcta caggcgttgt     300
agtttgtact ggtgacgaaa ctcagtgtta cggtacatgg ttcctattg gcttgctat      360 ccctgaaaat gagggtggtg ctctgaggg tggcggttct gagggtggcg ctctgaggg      420 tggcggtact aaacctcctg agtacggtga tacacctatt ccgggctata cttatatcaa     480
ccctctcgac ggcacttatc cgcctggtac tgagcaaaac cccgctaatc ctaatccttc     540
tcttgaggag tctcagcctc ttaatacttt catgtttcag aataataggt tccgaaatag     600
gcagggggca ttaactgttt atacgggcac tgttactcaa ggcactgacc ccgttaaaac     660
ttattaccag tacactcctg tatcatcaaa agccatgtat gacgcttact ggaacggtaa     720
attcagagac tgcgctttcc attctggctt taatgaggat ccattcgttt gtgaatatca     780
aggccaatcg tctgacctgc ctcaacctcc tgtcaatgct ggcggcggct ctggtggtgg     840
ttctggtggc ggctctgagg gtggcggctc tgagggtggc ggttctgagg gtggcggctc     900
tgagggtggc ggttccggtg cggctccggt tccggtgat tttgattatg aaaaaatggc     960
aaacgctaat aaggggggcta tgaccgaaaa tgccgatgaa aacgcgctac agtctgacgc    1020
taaaggcaaa cttgattctg tcgctactga ttacggtgct gctatcgatg gtttcattgg    1080
tgacgtttcc ggccttgcta atggtaatgg tgctactggt gattttgctg gctctaattc    1140
ccaaatggct caagtcggtg acggtgataa ttcacctta atgaataatt tccgtcaata    1200
tttaccttct ttgcctcagt cggttgaatg tcgcccttat gtctttggcg ctggtaaacc    1260
atatgaattt tctattgatt gtgacaaaat aaacttattc cgtggtgtct ttgcgttct    1320 tttatatgtt gccaccttta tgtatgtatt ttcgacgttt gctaacatac tgcgtaataa    1380
ggagtcttaa gtaatctaga taacgagggc aaaaaatgaa aaagacagct atcgcgattg    1440
cagtggcact ggctggtttc gctaccgtag cgcaggccga tatcgtgctg acccagagcc    1500 cggcgacccct gagcctgtct ccgggcgaac gtgcgaccct gagctgcaga gcgagccagt    1560
ctgtttctcg ttcttatctg gcttggtacc agcagaaacc aggtcaagca ccgcgtctat    1620
taatttatgg tgcttctcgt cgtgcaactg gggtcccggc gcgttttagc ggctctggat    1680
```

```
ccggcacgga ttttaccctg accattagca gcctggaacc tgaagacttt gcgacttatt    1740
attgccagca gcgtggtaat tattctatta cctttggcca gggtacgaaa gttgaaatta    1800
aacgtacggt ggctgctccg agcgtgttta ttttccgcc gagcgatgaa caactgaaaa     1860
gcggcacggc gagcgtggtg tgcctgctga acaaccttta tccgcgtgaa gcgaaagttc    1920
agtggaaagt agacaacgcg ctgcaaagcg gcaacagcca ggaaagcgtg accgaacagg    1980
atagcaaaga tagcacctat tctctgagca gcaccctgac cctgagcaaa gcggattatg    2040
aaaaacataa agtgtatgcg tgcgaagtga cccatcaagg tctgagcagc ccggtgacta    2100
aatcttttaa tcgtggcgag gcctgataag catgcgtagg agaaaataaa atgaaacaaa    2160
gcactattgc actggcactc ttaccgttgc tcttcacccc tgttaccaaa gcccaggtgc    2220
aattggtgga aagcggcggc ggcctggtgc aaccgggcgg cagcctgcgt ctgagctgcg    2280
cggcctccgg atttaccttt tcttcttatg gtggtaattg ggtgcgccaa gcccctggga    2340
agggtctcga gtgggtgagc ggtatccatt attctggtag ctctacctat tatgcggata    2400
gcgtgaaagg ccgttttacc atttcacgtg ataattcgaa aaacaccctg tatctgcaaa    2460
tgaacagcct gcgtgcggaa gatacggccg tgtattattg cgcgcgtgct cttcataagt    2520
gggctggttg gggttttgat cattgggggcc aaggcaccct ggtgacggtt agctcagcgt    2580
cgaccaaagg tccaagcgtg tttccgctgg ctccgagcag caaaagcacc agcggcggca    2640
cggctgccct gggctgcctg gttaaagatt atttcccgga accagtcacc gtgagctgga    2700
acagcggggc gctgaccagc ggcgtgcata ccttccgc ggtgctgcaa agcagcggcc    2760
tgtatagcct gagcagcgtt gtgaccgtgc cgagcagcag cttaggcact cagacctata    2820
tttgcaacgt gaaccataaa ccgagcaaca ccaaagtgga taaaaagtg gaaccgaaaa    2880 gcgaattccc agggggagc ggaggtgcgc cgcaccatca tcaccatcac tgctgataag    2940
cttgacctgt gaagtgaaaa atggcgcaga ttgtgcgaca ttttttttgt ctgccgttta    3000
atgaaattgt aaacgttaat attttgttaa aattcgcgtt aaattttgt taaatcagct    3060 cattttttaa ccaataggcc gaaatcggca aaatccctta taaatcaaaa gaatagaccg    3120
agatagggtt gagtgttgtt ccagtttgga acaagagtcc actattaaag aacgtggact    3180
ccaacgtcaa agggcgaaaa accgtctatc agggcgatgg cccactacga gaaccatcac    3240
cctaatcaag ttttttgggg tcgaggtgcc gtaaagcact aaatcggaac cctaaaggga    3300
gcccccgatt tagagcttga cggggaaagc cggcgaacgt ggcgagaaag gaagggaaga    3360
aagcgaaagg agcgggcgct agggcgctgg caagtgtagc ggtcacgctg cgcgtaacca    3420
ccacacccgc cgcgcttaat gcgccgctac agggcgcgtg ctagccatgt gagcaaaagg    3480
ccagcaaaag gccaggaacc gtaaaaaggc cgcgttgctg gcgttttcc ataggctccg    3540 ccccctgac gagcatcaca aaaatcgacg ctcaagtcag aggtggcgaa acccgacagg    3600
actataaaga taccaggcgt ttccccctgg aagctccctc gtgcgctctc ctgttccgac    3660
cctgccgctt accggatacc tgtccgcctt tctcccttcg ggaagcgtgg cgctttctca    3720
tagctcacgc tgtaggtatc tcagttcggt gtaggtcgtt cgctccaagc tgggctgtgt    3780
gcacgaaccc ccgttcagt ccgaccgctg cgccttatcc ggtaactatc gtcttgagtc    3840
caacccggta agacacgact tatcgccact ggcagcagcc actggtaaca ggattagcag    3900
agcgaggtat gtaggcggtg ctacagagtt cttgaagtgg tggcctaact acggctacac    3960
tagaagaaca gtatttggta tctgcgctct gctgtagcca gttaccttcg gaaaaagagt    4020
```

```
tggtagctct tgatccggca aacaaaccac cgctggtagc ggtggttttt ttgtttgcaa    4080
gcagcagatt acgcgcagaa aaaaaggatc tcaagaagat cctttgatct tttctacggg    4140
gtctgacgct cagtggaacg aaaactcacg ttaagggatt ttggtcagat ctagcaccag    4200
gcgtttaagg gcaccaataa ctgccttaaa aaaattacgc cccgccctgc cactcatcgc    4260
agtactgttg taattcatta agcattctgc cgacatggaa gccatcacaa acggcatgat    4320
gaacctgaat cgccagcggc atcagcacct tgtcgccttg cgtataatat ttgcccatag    4380
tgaaaacggg ggcgaagaag ttgtccatat tggctacgtt taaatcaaaa ctggtgaaac    4440
tcacccaggg attggctgag acgaaaaaca tattctcaat aaacccttta gggaaatagg    4500
ccaggttttc accgtaacac gccacatctt gcgaatatat gtgtagaaac tgccggaaat    4560
cgtcgtggta ttcactccag agcgatgaaa acgtttcagt ttgctcatgg aaaacggtgt    4620
aacaagggtg aacactatcc catatcacca gctcaccgtc tttcattgcc atacggaact    4680
ccgggtgagc attcatcagg cgggcaagaa tgtgaataaa ggccggataa aacttgtgct    4740
tatttttctt tacggtcttt aaaaaggccg taatatccag ctgaacggtc tggttatagg    4800
tacattgagc aactgactga aatgcctcaa aatgttcttt acgatgccat tgggatatat    4860
caacggtggt atatccagtg atttttttct ccattttagc ttccttagct cctgaaaatc    4920
tcgataactc aaaaaatacg cccggtagtg atcttatttc attatggtga agttggaac     4980 ctcacccgac gtctaatgtg agttagctca ctcattaggc accccaggct ttacacttta    5040
tgcttccgg                                                            5049
```

METHODS FOR THE FORMATION OF DISULPHIDE BONDS

CROSS-REFERENCE TO RELATED APPLICATION

This application claims the benefit of U.S. provisional application Ser. No. 60/989,035 filed Nov. 19, 2007 and U.S. provisional application Ser. No. 60/957,027 filed Aug. 21, 2007, which are both incorporated by reference in their entireties.

A number of documents are cited throughout this specification. The disclosure content of these documents is herewith incorporated by reference in their entirety.

BACKGROUND OF THE INVENTION

In 1985, Smith first demonstrated that filamentous phages tolerate foreign protein fragments inserted in their gene III protein (pIII), and could show that the protein fragments are presented on the phage surface (Smith, 1985). Ladner extended this concept to the screening of repertoires of (poly) peptides and/or proteins displayed on the surface of phage particles (WO 88/06630; WO 90/02809). Since then, phage display has experienced a dramatic progress and resulted in substantial achievements.

Various formats have been developed to construct and screen (poly)peptide/protein phage-display libraries, and a large number of review articles and monographs cover and summarise these developments (e.g., Kay et al., 1996; Dunn, 1996; McGregor, 1996). Most often, filamentous phage-based systems have been used.

Initially proposed as display of single-chain Fv (scFv) fragments (WO 88/06630; see also WO 92/01047), the method has rapidly been expanded to the display of other (poly)peptides/proteins, such as bovine pancreatic trypsin inhibitor (BPTI) (WO 90/02809), peptide libraries (WO 91/19818), human growth hormone (WO 92/09690), and various other proteins, including the display of multimeric proteins such as Fab fragments (WO 91/17271; WO 92/01047).

To anchor the (poly)peptides/proteins to the filamentous bacteriophage surface, mostly genetic fusions to phage coat proteins are employed. Preferred are fusions to gene III protein (Parmley & Smith, 1988) or fragments thereof (Bass et al., 1990), and gene VIII protein (Greenwood et al., 1991). In one case, gene VI has been used (Jespers et al., 1995), and in one case, a combination of gene VII and gene IX has been used for the display of Fv fragments (Gao et al., 1999).

Furthermore, phage display has also been achieved on phage lambda. In that case, gene V protein (Maruyama et al., 1994), gene J protein, and gene D protein (Sternberg & Hoess, 1995; Mikawa et al., 1996) have been used.

Besides using genetic fusions, foreign peptides or proteins have been attached to phage surfaces via association domains. In WO 91/17271, it was suggested to use a tag displayed on phage and a tag-binding ligand fused to the (poly)peptide/protein to be displayed to achieve a non-covalent display.

A similar concept was pursued for the display of cDNA libraries (Crameri & Suter, 1993). There, the jun/fos interaction was used to mediate the display of cDNA fragments. In their construct, additional cysteine residues flanking both ends of jun as well as fos further stabilised the interaction by forming two disulfide bonds.

One question used to be, how to best recover phages which have bound to the desired target. Normally, this is achieved by elution with appropriate buffers, either by using a pH- or salt gradient, or by specific elution using soluble target. However, the most interesting binders which bind with high affinity to the target might be lost by that approach. Several alternative methods have been described which try to overcome that problem, either by providing a cleavage signal between the (poly)peptide/protein being displayed and its fusion partner, or between the target of interest and its carrier which anchors the target to a solid surface. Furthermore, most of the approaches referred to hereinabove require the use of fusion proteins comprising at least part of a phage coat protein and a foreign (poly)peptide/protein.

In WO 01/05909, an entirely different system is described which does not require fusion proteins, and hence solved many of these problems. The so-called "CysDisplay" system, described in WO 01/05909, is based on the formation of a covalent disulphide bond between a bacteriophage coat protein and an immunoglobulin or a functional fragment thereof. The immunoglobulin, or the functional fragment thereof, is displayed on the surface of a bacteriophage particle. A similar technology was subsequently disclosed in WO 03/060065. WO 03/060065 differs from WO 01/05909 in that the Cys-tagged pIII polypeptide is provided via a modified helper phage rather than a phagemid. Furthermore, WO 03/060065 also mentions other adapters that might be employed to display (poly)peptides/proteins on bacteriophage particles, such as homomultimeric proteins (PDGF, Max, RelA, neurotrophin) and heteromultimeric proteins (proteink kinase complexes, SH2-domain conating proteins, a-Pal/Max, Hox/Pbx).

Although the CysDisplay system is functioning well, a system which displays higher amounts of the (poly)peptides/proteins on the bacteriophage particles can be advantageous in certain situations, for example, such an improved system with increased display rates, in particular an increased functional display rate, would surely be beneficial and enable the more convenient, reliable and specific isolation of binders, in particular binders which bind to their target with high affinity.

Snyder et al., 1981, investigated the local environment of reactive cysteine residues of peptides of naturally occurring proteins by treatment with 2-nitrobenzoic acid and observed that cysteine residues surrounded by positively charged amino acids showed higher reactivity. In a follow up study Snyder et al., 1983, investigated the kinetics of disulfide formation and came to essentially the same conclusions. Bulaj et al., 1998, investigated the kinetics of 16 model peptides for their capability to form disulphide bond with various non-proteinaceous molecules. They observed that the presence of net charges on the peptides and on the non-proteinaceous reagents have influence on the reactivity. Britto et al., 2002, investigated the electrostatic environment of intramolecular disulphide bonds in tubulin and found that the most reactive cysteine residues were within 6.5 Angstrom of positively charged residues, presumably promoting dissociation of the thiol to the thiolate anion. Hansen et al., 2005, investigated intramolecular disulphide bonds of engineered YFP and found an increase in reactivity if positively charged amino acids are present in the proximity of the reactive cysteine residues. Albrecht et al., 2006, reported the generation of monospecific multivalent Fab's attached to PEG via cysteine residues.

However, none of the studies above describe a system in which an intermolecular disulphide bond is formed between a first (poly)peptide/protein and a second, different, (poly)peptide/protein. In particular, in none of these studies is such a disulphide bond formed in the periplasmatic space of a host cell. Furthermore, in none of the cited studies is a (poly) peptide/protein displayed on the surface of a bacteriophage particle.

SUMMARY OF THE INVENTION

Thus, the present invention provides an improved method for the formation of a disulphide bond between a first cysteine residue comprised in a first (poly)peptide/protein and a second cysteine residue comprised in a second (poly)peptide/protein, preferably a different (poly)peptide/protein. Said improvement shall preferably lead to a higher reactivity of said cysteine residues, thereby conferring an increased display rate, in particular a, increased functional display rate.

The solution to this technical problem is achieved by providing the embodiments characterised in the claims. The technical solution that solves the underlying problem and which forms the basis of the present invention, i.e. introducing positively charged amino acids in spatial context to the reactive cysteine residues, is neither provided nor suggested in the prior art.

In particular embodiments, the present invention provides an improved system for the display of (poly)peptides/proteins on the surface of bacteriophage particles without the need to use fusion proteins with phage coat proteins. The higher reactivity of said cysteine residues thereby leads to a higher display rate, in particular a higher functional display rate.

Accordingly, the present invention provides, among other things, an improved method to screen large libraries of (poly) peptides/proteins displayed on the surface of bacteriophage particles.

In certain embodiments the present invention provides a method to form a disulphide bond, comprising: causing or allowing the attachment of a first (poly)peptide/protein to a second (poly)peptide/protein, wherein said attachment is caused by the formation of a disulphide bond between a first cysteine residue comprised in said first (poly)peptide/protein and a second cysteine residue comprised in said second (poly) peptide/protein, wherein one of said (poly)peptides/proteins comprises an amino acid with a pI greater than 8 which positively affects the reactivity of at least one of said cysteine residues. Said amino acid with a pI greater than 8 may be comprised in said first (poly)peptide/protein or in said second (poly)peptide/protein. Said amino acid with a pI greater than 8 may not be present at a corresponding amino acid position in said wild type (poly)peptide/protein. Said amino acid with a pI greater than 8 may have been artificially introduced. Said amino acid with a pI greater than 8 may be comprised within ten amino acids adjacent to a cysteine residue on the same (poly)peptide/protein, preferably within five amino acids adjacent to a cysteine residue on the same (poly)peptide/protein. Said first cysteine residue may be present at or in the vicinity of the N-terminus or the C-terminus of said first (poly)peptide/protein. Said first cysteine residue may also be a N-terminal or a C-terminal cysteine residue. Said second cysteine residue may be present at or in the vicinity of the N-terminus or the C-terminus of said second (poly)peptide/protein. Said second cysteine residue may also be a N-terminal or a C-terminal cysteine residue. Said second (poly)peptide/protein may be displayed on the surface of a bacteriophage particle. Said first and said second (poly)peptide/protein may be expressed and assembled in an appropriate host cell. Said disulphide bond may be formed in the periplasmatic space of a host cell. Said disulphide bond may be a intermolecular disulphide bond. Said amino acid with a pI greater than 8 may be selected from lysine and arginine, preferably lysine. Said first (poly)peptide/protein and said second (poly)peptide/protein may be different. Said first (poly)peptide/protein may be a member of the protein coat of a bacteriophage particle. Said member of the protein coat may be a truncated variant of a wild type coat protein of a bacteriophage, wherein said truncated variant comprises at least that part of said wild type coat protein causing the incorporation of said coat protein into the protein coat of the bacteriophage particle. Said member of the protein coat may be a modified variant of a wild type coat protein of a bacteriophage, wherein said modified variant is capable of being incorporated into the protein coat of the bacteriophage particle. Said first cysteine residue comprised in said first (poly)peptide/protein may be present at a corresponding amino acid position in a wild type coat protein of a bacteriophage. Said first cysteine residue comprised in said first (poly)peptide/protein may not be present at a corresponding amino acid position in a wild type coat protein of a bacteriophage. Said first cysteine residue may have been artificially introduced into a wild type coat protein of a bacteriophage. Said first cysteine residue may have been artificially introduced into a truncated variant of a wild type coat protein of a bacteriophage. Said first cysteine residue may have been artificially introduced into a modified variant of a wild type coat protein of a bacteriophage. Said bacteriophage particle may be a bacteriophage particle of a filamentous bacteriophage. Said member of the protein coat of a bacteriophage particle may be or may be derived from the wild type coat protein pIII. Said member of the protein coat of the bacteriophage particle may be or may be derived from the wild type coat protein pIX. Said second cysteine residue comprised in said second (poly)peptide/protein may not be present at a corresponding amino acid position in the wild type of said second (poly)peptide/protein. Said second cysteine residue may have been artificially introduced into said second (poly)peptide/protein. Said second (poly)peptide/protein may comprise an immunoglobulin or a functional fragment thereof. Said functional fragment may be a scFv or Fab fragment.

In certain embodiments the present invention provides a method to display a second (poly)peptide/protein on the surface of a bacteriophage particle comprising: causing or allowing the attachment of said (poly)peptide/protein after expression to a member of the protein coat, wherein said attachment is caused by the formation of a disulphide bond between a first cysteine residue comprised in said member of the protein coat and a second cysteine residue comprised in said (poly)peptide/protein, wherein said (poly)peptide/protein or said member of the protein coat comprises an amino acid with a pI greater than 8 which positively affects the reactivity of said first or said second cysteine residue.

In certain embodiments the present invention provides a nucleic acid sequence encoding a modified variant of a wild type coat protein of a bacteriophage, wherein said modified variant comprises:

(a) one or more parts of said wild type coat protein of a bacteriophage, wherein one of said parts comprises at least that part which causes or allows the incorporation of said coat protein into the phage coat, (b) a first cysteine residue, and (c) an amino acid with a pI greater than 8 which positively affects the reactivity of said first cysteine residue.

In certain embodiments the present invention provides a nucleic acid sequence encoding a modified immunoglobulin or functional fragment thereof, wherein said modified immunoglobulin or a functional fragment comprises:

(a) an immunoglobulin or a functional fragment thereof, (b) a cysteine residue, and an amino acid with a pI greater than 8 which positively affects the reactivity of said cysteine residue. Said functional fragment of a modified immunoglobulin may be a scFv or Fab fragment.

Any of the aforementioned nucleic acid sequence may further encode one or more peptide sequences for purification and/or detection purposes.

In certain embodiments the present invention provides a vector comprising any of the aforementioned nucleic acid sequences. Said vector may further comprise one or more nucleic acid sequences encoding a second (poly)peptide/protein comprising a second cysteine residue.

In certain embodiments the present invention provides a host cell comprising any of the aforementioned nucleic acid sequences or vectors. Said host cell may comprise a second vector comprising one or more nucleic acid sequences encoding a second (poly)peptide/protein comprising a second cysteine residue.

In certain embodiments the present invention provides a (poly)peptide/protein encoded by any of the aforementioned nucleic acid sequences, encoded by any of the aforementioned vectors or produced by any of the aforementioned host cells.

In certain embodiments the present invention provides a bacteriophage particle displaying a (poly)peptide/protein on its surface obtainable the aforementioned methods. Said (poly)peptide/protein displayed on said bacteriophage particle may be a immunoglobulin or a functional fragment thereof.

In certain embodiments the present invention provides a diverse collection of bacteriophage particles as mentioned hereinabove, wherein each of said bacteriophage particles displays a second (poly)peptide/protein out of a diverse collection of second (poly)peptides/proteins.

In certain embodiments the present invention provides a method for obtaining a (poly)peptide/protein having a desired property, comprising:
  (a) providing a diverse collection of bacteriophage particles as described hereinabove, and
  (b) screening said diverse collection and/or selecting from said diverse collection to obtain at least one bacteriophage particle displaying a (poly)peptide/protein having a desired property. Step (b) of said method may further comprise:
  (ba) contacting said diverse collection of bacteriophage particles with the target of interest;
  (bb) eluting bacteriophage particles not binding to the target of interest; and
  (bc) eluting bacteriophage particles binding to the target of interest by treating the complexes of target of interest and bacteriophages binding to said target of interest formed under step (ba) under reducing conditions. Said desired property may be binding to a target of interest, inhibiting a target of interest, blocking a target of interest, activation of a target-mediated reaction or an enzymatic activity.

In certain embodiments the present invention provides a complex comprising
  a first (poly)peptide/protein comprising a first cysteine residue, and
  a second (poly)peptide/protein comprising a second cysteine residue,
  wherein one of said (poly)peptides/proteins further comprises an amino acid with a pI greater than 8 which positively effects the reactivity of at least one of said cysteines residues, and wherein said first and said second (poly)peptide/protein form a disulphide bond via said cysteine residues. Said second (poly)peptide/protein may be a member of a diverse collection of second (poly)peptides/proteins displayed on a diverse collection of a plurality of bacteriophage particles. Said first (poly)peptide/protein may be a phage coat protein. Said second (poly)peptides/protein may comprise an immunoglobulin or a functional fragment thereof. Said functional fragment may be a scFv or Fab fragment.

In certain embodiments the present invention provides a host cell comprising any of the aforementioned complexes.

In certain embodiments the present invention provides a method to form a disulphide bond, comprising: causing or allowing the attachment of a first (poly)peptide/protein to a second (poly)peptide/protein, wherein said attachment is caused by the formation of a disulphide bond between a first cysteine residue comprised in said first (poly)peptide/protein and a second cysteine residue comprised in said second (poly)peptide/protein, wherein one of said (poly)peptides/proteins comprises an amino acid with a pI greater than 8. Said amino acid with a pI greater than 8 may positively affects the reactivity of at least one of said cysteine residues.

DETAILED DESCRIPTION OF THE INVENTION

A "disulphide bond" is a covalent bond formed by the reaction of two thiol groups. Disulphide bonds play an important role in the folding and stability of (poly)peptides and proteins. Many proteins with disulphide bonds are secreted. Many cellular compartments are a reducing environment, and disulphide bonds are generally unstable in the cytosol. Disulphide bonds in (poly)peptides and proteins are typically formed between the thiol groups of cysteine residues, whereby the oxidation of two cysteine residues form a covalent disulphide bond. Disulphide bonds can be intra- or intermolecular bonds. In prokaryotes, disulphide bonds are preferably formed in the oxidizing environment of the periplasm. In eukaryotic cells, disulphide bonds are usually formed in the oxidative environment of the endoplasmic reticulum, but not in the reducing environment of the cytosol (with the exception of some cytosolic proteins that have cysteine residues that function as oxidation sensors). Disulphide bonds are mostly found in secretory proteins, lysosomal proteins, and the exoplasmic domains of membrane proteins. Disulphide bonds also play a significant role in the vulcanization of rubber.

The "pI" or "isoelectric point" is the pH at which a molecule, or a surface, carries no net electrical charge. In order to have a sharp isoelectric point, a molecule (or surface) must be amphoteric, i.e. it must have both acidic and basic functional groups. Proteins and amino acids are molecules that meet this requirement. The pI's of the twenty naturally occuring amino acids are listed in Table 1. However, non-naturally occurring amino acids may be used as well to practice the method of the present invention.

TABLE 1

| Isoelectric points (pI's) of the twenty naturally occurring amino acids (ordered by increasing pI) | |
|---|---|
| Amino acid | Isoelectric point (pI) |
| aspartic acid | 2.77 |
| glutamic acid | 3.22 |
| cysteine | 5.02 |
| asparagine | 5.41 |
| phenylalanine | 5.48 |
| threonine | 5.64 |
| glutamine | 5.65 |
| tyrosine | 5.66 |
| serine | 5.68 |
| methionine | 5.74 |

TABLE 1-continued

Isoelectric points (pI's) of the twenty naturally
occurring amino acids (ordered by increasing pI)

| Amino acid | Isoelectric point (pI) |
|---|---|
| tryptophan | 5.89 |
| isoleucine | 5.94 |
| valine | 5.96 |
| glycine | 5.97 |
| leucine | 5.98 |
| alanine | 6.00 |
| proline | 6.30 |
| histidine | 7.47 |
| lysine | 9.59 |
| arginine | 11.15 |

For amino acids with only one amine group and one carboxyl group, the pI can be calculated from the pKa's of this molecule. For amino acids with more than two ionizable groups, such as lysine, those two pKa's are used for the calculation of the pI which lose and gain a charge from the neutral form of the amino acid. Respective calculations are known to the skilled artisan and can be found in any biochemical textbook [e.g. Nelson D L, Cox M M (2004). Lehninger Principles of Biochemistry. W. H. Freeman; 4th edition].

Proteins can be separated according to their pI via isoelectric focussing. At a pH below the pI, proteins carry a net positive charge. Above the pI, proteins carry a net negative charge. The pH of an electrophoretic gel is determined by the buffer used for that gel. If the pH of the buffer is above the pI of the protein being run, the protein will migrate to the positive pole (negative charge is attracted to a positive pole). If the pH of the buffer is below the pI of the protein being run, the protein will migrate to the negative pole of the gel (positive charge is attracted to the negative pole). If the protein is run with a buffer pH that is equal to the pI, it will not migrate at all. This is also true for individual amino acids.

In preferred embodiments, the first and/or the second (poly)peptide/protein of the present invention comprises an amino acid with a pI greater than 8. In other preferred embodiments, said first and/or second (poly)peptide/protein comprises an amino acid with a pI greater than 9, greater than 10 or greater than 11. In other preferred embodiments, said amino acid with a pI greater than 8, greater than 9, greater than 10 or greater than 11 is present in the first (poly)peptide/protein. In alternative preferred embodiments, said amino acid with a pI greater than 8, greater than 9, greater than 10 or greater than 11 is present in the second (poly)peptide/protein. In other preferred embodiments, said amino acid with a pI greater than 8 is selected from lysine and arginine. In certain preferred embodiments, said amino acid is lysine. In alternative preferred embodiments, said amino acid is arginine.

In certain preferred embodiments, the first (poly)peptide/protein of the present invention comprises more than one amino acid with a pI greater than 8 which positively affects the reactivity of at least one of said cysteine residues. In alternative preferred embodiments, the second (poly)peptide/protein of the present invention comprises more than one amino acid with a pI greater than 8 which positively affects the reactivity of at least one of said cysteine residues. In some embodiments, said first and/or said second (poly)peptide/protein comprise at least two, at least three, at least four or at least five amino acids with a pI greater than 8 which positively affects the reactivity of at least one of said cysteine residues.

In even further embodiments, the amino acid residues directly adjacent to said amino acid with a pI greater than 8 are histidine residues. In certain embodiments, the amino acid residue directly N-terminal to said amino acid with a pI greater than 8 is a histidine residue. In other embodiments, the amino acid residue directly C-terminal to said amino acid with a pI greater than 8 is a histidine residue. In yet other embodiments, both, the amino acid residue directly N-terminal to said amino acid with a pI greater than 8 and the amino acid residue directly C-terminal to said amino acid with a pI greater than 8, are histidine residues. Further preferred stretches of polypeptides directly adjacent to said amino acid with a pI greater than 8 are polypeptides of the length of three, four, five, six, seven or eight histidine residues, wherein at least one histidine residue is substituted with an amino acid with a pI greater than 8, preferably lysine. Most preferred stretches of polypeptides directly adjacent to said amino acid with a pI greater than 8 are polypeptides of the length of six histidine residues, wherein one, two or three histidine residue are substituted with an amino acid with a pI greater than 8, preferably lysine. Particularly preferred are the following polypeptides directly adjacent to said amino acid with a pI greater than 8: HHHHHH, HHHKHH, HHHHHK, HKHKHK (all amino acids in one letter code, i.e. H=histidine, K=lysine). In certain embodiment the first and/or second cysteine residue comprised in said first and/or second (poly)peptide/protein is directly C-terminal to such a stretch of histidine residues, in which at least one histidine residue is substituted with an amino acid with a pI greater than 8, preferably lysine.

In other embodiments, the first and/or second cysteine residue comprised in said first and/or second (poly)peptide/protein is directly C-terminal to a stretch of three, four, five, six, seven or eight histidine residues and directly N-terminal to an amino acid with a pI greater than 8, preferably lysine. Optionally one of the histidine residues directly N-terminal to the first and/or second cysteine residue comprised in said first and/or second (poly)peptide/protein is additionally substituted with an amino acid with a pI greater than 8, preferably lysine.

The term "positively affects the reactivity" as used in the context of the present invention refers to a situation where the equilibrium of a reaction in which two thiol groups react to form a disulphide bond, is shifted towards the side of the product, i.e. a higher number of disulphide bonds is formed, e.g. as compared to known systems, such as, for example, the "CysDisplay" system described in WO 01/05909. The reactivity of the respective thiol groups can easily be detected and measured as described in WO 01/05909 and the present invention. The relative display rate or the functional display rate, as described hereinbelow, may be an appropriate test system. According to the present invention such a shift of the equilibrium is achieved via an amino acid with a pI greater than 8 which is present in one of the reactants, i.e. either the first or the second (poly)peptide/protein. Said amino acid with a pI greater than 8 is spatially located in the vicinity of the first cysteine residue comprised in the first (poly)peptide/protein or the second cysteine residue comprised in the second (poly)peptide/protein in a manner so that it can effect such shift of the equilibrium.

In some embodiments, said amino acid with a pI greater than 8 is located within the ten amino acids, preferably within the eight amino acids, more preferably within the six amino acids, and most preferably within the five amino acids directly adjacent to the said first or said second cysteine residue. In certain embodiments, said amino acid with a pI greater than 8 is present N-terminal to said first or said second cysteine residue. In other embodiments, said amino acid with a pI greater than 8 is present C-terminal to said first or said second cysteine residue.

In other embodiments, said amino acid with a pI greater than 8 is located more than ten amino acids distant from the first or the second cysteine residue comprised in said first or second (poly)peptide/protein, but said first or second (poly)peptide/protein has a three dimensional structure, so that said amino acid with a pI greater than 8 is brought into spatial proximity with said first or said second cysteine residue. The amino acid with a pI greater than 8 and the cysteine residue affected by said amino acid may be comprised on the same (poly)peptide/protein, for example on different domains of the same (poly)peptide/protein. Alternatively, the amino acid with a pI greater than 8 and the cysteine residue affected by said amino acid may be comprised on different (poly)peptides/proteins, e.g. the amino acid with a pI greater than 8 on the first (poly)peptide/protein and the cysteine residue affected by said amino acid on the second (poly)peptide/protein, or vice versa. In this case, the amino acid with a pI greater than 8 which is comprised on one (poly)peptide/protein positively affects the reactivity of the second cysteine residue comprised on the other (poly)peptide/protein. The skilled artisan will know which amino acid positions within a given (poly)peptide/protein may be chosen to introduce an amino acid with a pI greater than 8 that positively affect the reactivity of a cysteine residue. Various techniques for the determination of the three-dimensional structures of (poly)peptides/proteins are known, such as X-ray crystallography or NMR techniques. Furthermore, the three-dimensional structures of many (poly)peptides/proteins are already available, making the selection of appropriate amino acid positions easy. In particular, the three-dimensional structures of various immunoglobulins or functional fragments, such as scFv or Fab fragments are publicly available via various databases, such as PDB (http://www.rcsb.org/pdb/home/home.do) or PubMed (http://www.ncbi.nlm.nih.gov/sites/entrez?db=Structure).

In the context of the present invention, the term "bacteriophage" relates to bacterial viruses forming packages consisting of a protein coat containing nucleic acid required for the replication of the phages. The nucleic acid may be DNA or RNA, either double or single stranded, linear or circular. Bacteriophage such as phage lambda or filamentous phage (such as M13, fd, or f1) are well known to the artisan of ordinary skill in the art. In certain embodiments filamentous phages are preferred. In the context of the present invention, the term "bacteriophage particles" refers to the particles according to the present invention, i.e. to particles displaying a (poly)peptide/protein via a disulfide bond. In certain embodiments bacteriophage particles of filamentous phages are preferred.

During the assembly of bacteriophages, the coat proteins may package different nucleic acid sequences, provided that they comprise a packaging signal. In the context of the present invention, the term "nucleic acid sequences" contained in bacteriophages or bacteriophage particles relates to nucleic acid sequences or vectors having the ability to be packaged by bacteriophage coat proteins during assembly of bacteriophages or bacteriophage particles. Preferably said nucleic acid sequences or vectors are derived from naturally occurring genomes of bacteriophage, and comprise for example, in the case of filamentous phage, phage and phagemid vectors. The latter are plasmids containing a packaging signal and a phage origin of replication in addition to plasmid features.

In certain embodiments, said first or said second (poly)peptide/protein are displayed on the surface of a bacteriophage particle. In preferred embodiments the second (poly)peptide/protein is displayed on the surface of a bacteriophage particle. In alternative embodiments the first (poly)peptide/protein is displayed on the surface of a bacteriophage particle. Preferred are filamentous bacteriophage particles.

In certain embodiments, said first or said second (poly)peptide/protein is a member of the protein coat of a bacteriophage particle. In preferred embodiments, the first (poly)peptide/protein is a member of the protein coat of a bacteriophage particle. In alternative embodiments, the second (poly)peptide/protein is a member of the protein coat of a bacteriophage particle. In preferred embodiments, said member of the protein coat of the bacteriophage particle is or is derived from the wild type coat protein pIII. In other embodiment said member of the protein coat of the bacteriophage particle is or is derived from the wild type coat protein pIX.

In the context of the present invention, the term "is derived" refers to a modification, wherein the modified protein is capable of being incorporated into the protein coat of the bacteriophage particle. Preferably, those parts of the modified protein corresponding to the wild type protein exhibit an amino acid identity exceeding about 50%, about 60%, about 70%, preferably about 80%, and most preferably about 90% compared to the corresponding wild type sequence.

In a yet further preferred embodiment, the present invention relates to a method, wherein said member of the protein coat is a wild type coat protein of a bacteriophage.

The term "wild type coat protein" refers to those proteins forming the phage coat of naturally occurring bacteriophages. In the case of filamentous bacteriophage, said wild type proteins are gene III protein (pIII), gene VI protein (pVI), gene VII protein (pVII), gene VIII protein (pVIII), and gene IX protein (pIX). The sequences, including the differences between the closely related members of the filamentous bacteriophages such as f1, fd, and M13, are well known to one of ordinary skill in the art (see, e.g., Kay et al., 1996).

In a further preferred embodiment, said member of the protein coat is a modified variant of a wild type coat protein of a bacteriophage, wherein said modified variant is capable of being incorporated into the protein coat of the bacteriophage particle.

The term "modified variant" refers to proteins derived from the wild type proteins referred to above which are modified as compared to the wild type sequences. Such modification may include any amino acid substitution, amino acid deletion or incorporation of additional amino acids as compared to the wild type sequences. The term "modified variant" includes "truncated variants" as defined below.

Methods for achieving modification of a wild type protein according to the present invention are well known to one of ordinary skill in the art, and involve standard cloning and/or mutagenesis techniques. Methods for the construction of nucleic acid molecules encoding a modified variant of a wild type protein used in a method according to the present invention, for construction of vectors comprising said nucleic acid molecules, including the construction of phage and/or phagemid vectors, for introduction of said vectors into appropriately chosen host cells, for causing or allowing the expression of said modified protein are well-known in the art (see, e.g., Sambrook et al., 2001; Ausubel et al., 1999; Kay et al., 1996). To identify modified variants according to the present invention, a detection tag may be fused to the variant, and an assay may be set up to determine whether the variant is capable or being incorporated into the phage coat of bacteriophage particles formed in the presence of the variant.

In a further preferred embodiment, said member of the protein coat is a truncated variant of a wild type coat protein of a bacteriophage, wherein said truncated variant comprises at least that part of said wild type coat protein causing the incorporation of said coat protein into the protein coat of the bacteriophage particle.

The term "truncated variant" refers to proteins derived from the wild type proteins referred to above which are modified by deletion of at least part of the wild type sequences. This comprises variants such as truncated gene III protein variants which have been found in bacteriophage mutants (Crissman & Smith, 1984) or which have been generated in the course of standard phage display methods (e.g. Bass et al., 1990; Krebber, 1996). For example, said truncated variant may consist, or include, the C-terminal domain of the gene III protein. To identify truncated variants according to the present invention, a detection tag may be fused to the variant, and an assay may be set up to determine whether the variant is incorporated into the phage coat of bacteriophage particles formed in the presence of the variant.

By way of truncating a wild type protein by deleting a part of the wild type protein, a cysteine residue may become available which in the wild type protein was forming a disulfide bond with a second cysteine comprised in the deleted part.

The term "(poly)peptide" relates to molecules comprising one or more chains of multiple, i. e. two or more, amino acids linked via peptide bonds.

The term "protein" refers to (poly)peptides where at least part of the (poly)peptide has or is able to acquire a defined three-dimensional arrangement by forming secondary, tertiary, or quaternary structures within and/or between its (poly)peptide chain(s). This definition comprises proteins such as naturally occurring or at least partially artificial proteins, as well as fragments or domains of whole proteins, as long as these fragments or domains are able to acquire a defined three-dimensional arrangement as described above.

Examples of (poly)peptides/proteins consisting of one chain are single-chain Fv antibody fragments, and examples for (poly)peptides/proteins consisting of more chains are Fab antibody fragments.

When the first cysteine residue is located at the C-terminus of the first (poly)peptide/protein, the display format corresponds to the conventional display set-up with the C-terminus being genetically fused to the member of the phage coat protein. However, by using the N-terminus of the first (poly)peptide/protein, the display format can be reverted as in the pJuFO system of Crameri & Suter referred to above (Crameri & Suter, 1993).

The term "surface of a bacteriophage particle" refers to the part of a bacteriophage particle which is in contact with the medium the particle is contained in and which is accessible. The surface is determined by the proteins being part of the phage coat (the members of the protein coat of the particle) which is assembled during phage production in appropriate host cells.

The term "after expression" refers to the situation that the nucleic acid encoding said second (poly)peptide/protein is expressed in a host cell prior to attachment of the second (poly)peptide/protein to said coat, in contrast to approaches where nucleic acid encoding fusion proteins with bacteriophage coat proteins are being expressed. The expression of nucleic acid encoding said second (poly)peptide/protein and the step of causing or allowing the attachment may be performed in separated steps and/or environments. Preferably, however, expression and the step of causing or allowing the attachment are being performed sequentially in an appropriate host cell.

The term "wherein said attachment is caused by the formation of a disulfide bond" refers to a situation, wherein the disulfide bond is responsible for the attachment, and wherein no interaction domain for interaction with a second domain present in the second (poly)peptide/protein has been recombinantly fused to said member of the protein coat, as for example in the case of the pJuFo system (Crameri & Suter, 1993).

In a preferred embodiment, the bacteriophage particle displaying the second (poly)peptide/protein contains a nucleic acid sequence encoding the second (poly)peptide/protein.

Methods for construction of nucleic acid molecules encoding a (poly)peptides/proteins according to the present invention, for construction of vectors comprising said nucleic acid molecules, for introduction of said vectors into appropriately chosen host cells, for causing or allowing the expression of said (poly)peptides/proteins are well-known in the art (see, e.g., Sambrook et al., 2001; Ausubel et al., 1999; Ge et al, 1995). Further well-known are methods for the introduction of genetic material required for the generation of progeny bacteriophages or bacteriophage particles in appropriate host cells, and for causing or allowing the generation of said progeny bacteriophages or bacteriophage particles (see, e.g., Kay et al., 1996).

In a certain embodiment, the present invention relates to a method, wherein said first cysteine residue is present at a corresponding amino acid position in the wild type version of said first (poly)peptide/protein. More preferably said first cysteine residue is present at a corresponding amino acid position in a wild type coat protein of a bacteriophage.

In a more preferred embodiment, said first cysteine residue is not present at a corresponding amino acid position in the wild type version of said first (poly)peptide/protein. Even more preferably said first cysteine residue is not present at a corresponding amino acid position in a wild type coat protein of a bacteriophage.

In the context of the present invention, the term "wild type version" of a (poly)peptide/protein refers to a (poly)peptide/protein having a naturally occurring amino acid sequence.

In a even more preferred embodiment, said first cysteine residue has been artificially introduced into a first (poly)peptide/protein. In more preferred embodiments said first cysteine residues has been artificially introduced into a wild type coat protein of a bacteriophage. In other embodiments said first cysteine residues has been artificially introduced into a modified variant of a wild type coat protein of a bacteriophage. In yet other embodiments said first cysteine residues has been artificially introduced into a truncated variant of a wild type coat protein of a bacteriophage.

In a certain embodiment, the present invention relates to a method, wherein said second cysteine residue is present at a corresponding amino acid position in the wild type version of said second (poly)peptide/protein. More preferably said second cysteine residue is present at a corresponding amino acid position in a immunoglobulin or a functional fragment thereof.

In a more preferred embodiment, said second cysteine residue is not present at a corresponding amino acid position in the wild type version of said second (poly)peptide/protein. Even more preferably, said second cysteine residue is not present at a corresponding amino acid position in a wild type coat protein of a bacteriophage.

In a even more preferred embodiment, said second cysteine residue has been artificially introduced into a second (poly)

peptide/protein. In more preferred embodiments, said second cysteine residues has been artificially introduced into an immunoglobulin or a functional fragment thereof. Preferably, said functional fragment is a scFv or Fab fragment.

In a certain embodiment, the present invention relates to a method, wherein said amino acid with a pI greater than 8 is present at a corresponding amino acid position in the wild type version of the first or the second (poly)peptide/protein. More preferably, said amino acid with a pI greater than 8 is present at a corresponding amino acid position in a wild type coat protein of a bacteriophage or an immunoglobulin or a functional fragment thereof, preferably a scFv or Fab fragment.

In a more preferred embodiment, said amino acid with a pI greater than 8 is not present at a corresponding amino acid position in the wild type version of the first or the second (poly)peptide/protein. In another preferred embodiment, said first (poly)peptide/protein is not a wild-type (poly)peptide/protein and said amino acid with a pI greater than 8 is not present in the wild-type version of said first (poly)peptide/protein. In another preferred embodiment, said second (poly)peptide/protein is not a wild-type (poly)peptide/protein and said amino acid with a pI greater than 8 is not present in the wild-type version of said second (poly)peptide/protein. Even more preferably, said amino acid with a pI greater than 8 is not present at a corresponding amino acid position in a wild type coat protein of a bacteriophage or an immunoglobulin or a functional fragment thereof, preferably a scFv or Fab fragment.

In a even more preferred embodiment, said amino acid with a pI greater than 8 has been artificially introduced into the wild type version of the first or the second (poly)peptide/protein. In more preferred embodiments, said amino acid with a pI greater than 8 has been artificially introduced into a wild type coat protein of a bacteriophage or an immunoglobulin or a functional fragment thereof, preferably a scFv or Fab fragment.

In the context of the present invention, the term "artificially introduced" refers to a situation where a (poly)peptide/protein has been modified by e.g. recombinant means. In the present invention, various (poly)peptide/protein may be modified. For example, the nucleic acid encoding the first (poly)peptide/protein may be manipulated by standard procedures to introduce a cysteine codon, creating a nucleic acid sequence encoding a modified first (poly)peptide/protein, wherein a cysteine residue is artificially introduced by insertion into, or addition of said cysteine residue to, said first (poly)peptide/protein, or by substitution of an amino acid residue comprised in said first (poly)peptide/protein or modified protein by said cysteine residue, or by fusion of said first (poly)peptide/protein with a second (poly)peptide/protein comprising said second cysteine residue, or by any combination of said insertions, additions, substitutions or fusions. Most preferably, said first (poly)peptide/protein is a wild type coat protein of a bacteriophage, or a modified or truncated variant thereof.

Likewise, the nucleic acid encoding the second (poly)peptide/protein may be manipulated by standard procedures to introduce a cysteine codon in the same manner as described for the first (poly)peptide/protein. Preferred said second (poly)peptide/protein comprises an immunoglobulin or a functional fragment thereof. Particularly preferred is a scFv or Fab fragment.

Likewise, the nucleic acid encoding the first or the second (poly)peptide/protein may be manipulated by standard procedures to introduce an amino acid codon, encoding for an amino acid with a pI greater than 8.

In the case where the first (poly)peptide/protein is a wild type coat protein of a bacteriophage, expression of the nucleic acid comprising such a recombinantly introduced cysteine codon, leads to the formation of a variant of the wild type coat protein comprising a cysteine residue.

In a further most preferred embodiment, said first cysteine has been artificially introduced into a truncated variant of a wild type coat protein of a bacteriophage.

In a yet further preferred embodiment, said first cysteine has been artificially introduced into a modified variant of a wild type coat protein of a bacteriophage.

Methods for achieving the artificial introduction according to the present invention are well-known to one of ordinary skill in the art, and involve standard cloning and/or mutagenesis techniques. Methods for the construction of nucleic acid molecules encoding a modified variant of a wild type protein used in a method according to the present invention, for construction of vectors comprising said nucleic acid molecules, for introduction of said vectors into appropriately chosen host cells, for causing or achieving the expression of said fusion proteins are well-known in the art (see, e.g., Sambrook et al., 2001; Ausubel et al., 1999).

In another embodiment, the present invention relates to a method, wherein said first cysteine residue is present at, or in the vicinity of, the C- or the N-terminus of said member of the first (poly)peptide/protein. In preferred embodiments, said first cysteine residue is present at, or in the vicinity of, the C- or the N-terminus of a member of the protein coat of a bacteriophage particle. In certain embodiments said first cysteine residue is a N-terminal cysteine residue. In other embodiments, said first cysteine residue is a C-terminal cysteine residue.

In another embodiment, the present invention relates to a method, wherein said second cysteine residue is present at, or in the vicinity of, the C- or the N-terminus of said member of the second (poly)peptide/protein. In preferred embodiments, said second cysteine residue is present at, or in the vicinity of, the C- or the N-terminus of an immunoglobulin, or a functional fragment thereof, preferably a scFv or Fab fragment. In certain embodiments, said second cysteine residue is a N-terminal cysteine residue. In other embodiments said second cysteine residue is a C-terminal cysteine residue.

The term "in the vicinity of" refers to a stretch of up to 15, more preferably, up to 10 amino acids, and, even more preferably, up to 5 amino acids, counted in both cases from either N- or C-terminus of said first or second (poly)peptide/protein.

In preferred embodiments, said first (poly)peptide/protein comprises a member of the protein coat of a bacteriophage particle, preferably pIII.

In preferred embodiments, said second (poly)peptide/protein comprises an immunoglobulin or a functional fragment thereof, preferably a scFv or Fab fragment.

In this context, "immunoglobulin" is used as a synonym for "antibody". The term "functional fragment" refers to a fragment of an immunoglobulin which retains the antigen-binding moiety of an immunoglobulin. Functional immunoglobulin fragments according to the present invention may be Fv (Skerra & Plückthun, 1988), scFv (Bird et al., 1988; Huston et al., 1988), disulfide-linked Fv (Glockshuber et al., 1992; Brinkmann et al., 1993), Fab, F(ab')2 fragments or other fragments well-known to the practitioner skilled in the art, which comprise the variable domain of an immunoglobulin or immunoglobulin fragment. Particularly preferred is an scFv or Fab fragment.

In certain embodiments, said first (poly)peptide/protein and said second (poly)peptide/protein are different. "Different" in this context means that the two (poly)peptides/proteins are not completely identical. In preferred embodiments said first (poly)peptide/protein is not a modified variant or a truncated variant of said second (poly)peptide/protein. In most preferred embodiments the first and the second (poly)peptide/protein encode for different functional (poly)peptides/proteins, e.g. one (poly)peptide/protein encodes for a modified variant of a wild type coat protein of a bacteriophage and the other (poly)peptide encodes for a immunoglobuline or a functional fragment thereof. In other preferred embodiments the first and the second (poly)peptide/protein are derived from different species (e.g. one (poly)peptide/protein is derived from a bacteriophage and the other (poly)peptide is derived from a human.

In preferred embodiments, the present invention provides a method to display a second (poly)peptide/protein on the surface of a bacteriophage particle comprising: causing or allowing the attachment of said second (poly)peptide/protein after expression to a member of the protein coat, wherein said attachment is caused by the formation of a disulphide bond between a first cysteine residue comprised in said member of the protein coat and a second cysteine residue comprised in said second (poly)peptide/protein, wherein said second (poly)peptide/protein comprises an amino acid with a pI greater than 8 which positively affects the reactivity of said first cysteine residue.

In other preferred embodiments, said first and said second (poly)peptide/protein are expressed and assembled in an appropriate host cell.

In yet a further embodiment, the present invention provides a method comprising the following steps:

(a) providing a host cell harbouring a first nucleic acid sequence comprising a first nucleic acid sequence encoding a first (poly)peptide/protein comprising a first cysteine residue and a second nucleic acid sequence comprising a second nucleic acid sequence encoding a second (poly)peptide/protein comprising a second cysteine residue, wherein one of said (poly)peptides/proteins comprises an amino acid with a pI greater than 8 which positively affects the reactivity of at least one of said cysteine residues;

(b) causing or allowing the expression of said first and said second nucleic acid sequences; and (c) causing or allowing the attachment of said first cysteine residue comprised in said first (poly)peptide/protein to said second cysteine residue comprised in said second (poly)peptide/protein.

The steps (b) and (c) may be performed sequentially, in either order or simultaneously.

In the context of the present invention, the term "causing or allowing the expression" describes cultivating host cells under conditions such that a nucleic acid sequence is expressed.

Methods for construction of nucleic acid molecules encoding a first or a second (poly)peptide/protein according to the present invention, for construction of vectors comprising said nucleic acid molecules, for introduction of said vectors into appropriately chosen host cells, for causing or allowing the expression of (poly)peptides/proteins are well-known in the art (see, e.g., Sambrook et al., 2001; Ausubel et al., 1999). Further well-known are methods for the introduction of genetic material required for the generation of progeny bacteriophages or bacteriophage particles in appropriate host cells, and for causing or allowing the generation of said progeny bacteriophages or bacteriophage particles (see, e.g., Kay et al., 1996). The step of causing or allowing the production of bacteriophage particles may require the use of appropriate helper phages, e.g. in the case of working with phagemids.

In a preferred embodiment, the present invention relates to a nucleic acid sequence encoding a modified variant of a wild type coat protein of a bacteriophage, wherein said modified variant comprises or consists of:

(a) one or more parts of said wild type coat protein of a bacteriophage, wherein one of said parts comprises at least that part which causes or allows the incorporation of said coat protein into the phage coat;

(b) a first cysteine residue, and (c) an amino acid with a pI greater than 8 which positively affects the reactivity of said first cysteine residue. In another embodiment, said amino acid with a pI greater than 8 positively affects the reactivity of a second cysteine residues comprised in a second (poly)peptide/protein. In preferred embodiments said nucleic acid sequence is an isolated nucleic acid sequence. In other embodiments said nucleic acid sequence further encodes for one or more peptide sequences for purification and/or detection purposes.

In another preferred embodiment, the present invention relates to a nucleic acid sequence encoding a modified immunoglobulin or a functional fragment thereof, wherein said modified immunoglobulin or functional fragment consists of (a) an immunoglobulin or a functional fragment thereof, (b) a cysteine residue, and (c) an amino acid with a pI greater than 8 which positively affects the reactivity of said cysteine residue. As used in this context, the immunoglobulin or a functional fragment thereof is equivalent to the second (poly)peptide/protein according to the terminology of the present invention. In another embodiment, said amino acid with a pI greater than 8 positively affects the reactivity of a another cysteine residues comprised in another (poly)peptide/protein. This other poly(peptide)/protein is equivalent to the first (poly)peptide/protein according to the terminology of the present invention. In preferred embodiments, said functional fragment of a modified immunoglobulin is a scFv or Fab fragment. In preferred embodiments said nucleic acid sequence is an isolated nucleic acid sequence. In other embodiments said nucleic acid sequence further encodes for one or more peptide sequences for purification and/or detection purposes.

In the context of the present invention, a modified variant obtained by substitution of an amino acid residue in a wild type coat protein sequence by a cysteine residue may be regarded as a variant composed of two parts of said wild type protein linked by an additional cysteine residue. Correspondingly, variants of a wild type coat protein comprising several mutations compared to the wild type sequence may be regarded as being composed of several wild type parts, wherein the individual parts are linked by the mutated residues. However, said variant may also result from the addition of up to six residues, including a cysteine residue, to either C- and or N-terminus of the wild type coat protein.

Likewise, a modified variant of an immunoglobulin or a functional fragment thereof obtained by substitution of an amino acid residue in a wild type or parental immunoglobulin protein sequence or a functional fragment thereof may be regarded as a variant composed of two parts of immunoglobulin or functional fragment linked by an additional cysteine residue. In the same manner a modified variant of a wild type coat protein or a modified variant of an immunoglobulin or a functional fragment thereof may be regarded as variants composed of two parts linked by an additional amino acid with a pI greater than 8 which positively affects the reactivity of said cysteine residue. When both, a cysteine residue and an amino acid with a pI greater than 8 are introduced into a modified variant of a wild type coat protein or a modified variant of an immunoglobulin or a functional fragment thereof, then said protein may be regarded as variants composed of three parts, or of even more parts, if said proteins comprise even more mutations.

In some embodiments, the nucleic acid sequence of the present invention further encodes for one or more peptide sequences for purification and/or detection purposes. In certain embodiments of the present invention the nucleic acid sequences of the present invention are comprised in a host cell.

Particularly preferred are peptides comprising at least five histidine residues (Hochuli et al., 1988), which are able to bind to metal ions, and can therefore be used for the purification of the protein to which they are fused (Lindner et al., 1992). Also provided for by the invention are additional moieties such as the commonly used c-myc and FLAG tags (Hopp et al., 1988; Knappik & Plückthun, 1994), the Strep-tag (Schmidt & Skerra, 1994; Schmidt et al., 1996), or the E-tag (GE Healthcare).

The modified variant of the first and the second (poly)peptide/protein of the present invention may further comprise amino acid residues required for cloning, for expression, or protein transport. Amino acid residues required for cloning may include residues encoded by nucleic acid sequences comprising recognition sequences for restriction endonucleases which are incorporated in order to enable the cloning of the nucleic acid sequences into appropriate vectors. Amino acid residues required for expression may include residues leading to increased solubility or stability of the (poly)peptide/protein. Amino acid residues required for protein transport may include signalling sequences responsible for the transport of the modified variant to the periplasm of *E. coli*, and/or amino acid residues facilitating the efficient cleavage of said signalling sequences. Further amino acid residues required for cloning, expression, protein transport, purification and/or detection purposes referred to above are numerous moieties well known to the practitioner skilled in the art.

In another embodiment, the present invention relates to a vector comprising a nucleic acid sequence according to the present invention.

In a preferred embodiment, the vector comprises or consists of one or more nucleic acid sequences encoding a modified variant of a wild type coat protein of a bacteriophage, wherein said modified variant comprises or consists of:
  (a) one or more parts of said wild type coat protein of a bacteriophage, wherein one of said parts comprises at least that part which causes or allows the incorporation of said coat protein into the phage coat;
  (b) a first cysteine residue, and
  (c) an amino acid with a pI greater than 8 which positively affects the reactivity of said first cysteine residue. In further embodiments said vector further comprises a nucleic acid sequence encoding a modified immunoglobulin or functional fragment thereof, wherein said modified immunoglobulin or a functional fragment consists of
  (a) an immunoglobulin or a functional fragment thereof, and
  (b) a second cysteine residue.

In a preferred embodiment, the vector comprises or consists of one or more nucleic acid sequences encoding a modified immunoglobulin or functional fragment thereof, wherein said modified immunoglobulin or a functional fragment comprises or consists of
  (a) an immunoglobulin or a functional fragment thereof,
  (b) a cysteine residue, and
  (c) an amino acid with a pI greater than 8 which positively affects the reactivity of said cysteine residue. In further embodiments, said vector further comprises a nucleic acid sequence encoding a modified variant of a wild type coat protein of a bacteriophage, wherein said modified variant comprises or consists of:
  (a) one or more parts of said wild type coat protein of a bacteriophage, wherein one of said parts comprises at least that part which causes or allows the incorporation of said coat protein into the phage coat; and
  (b) another cysteine residue.

In certain embodiments of the present invention, the vectors of the present invention are comprised in a host cell.

In a most preferred embodiment, said second (poly)peptide/protein comprises an immunoglobulin or a functional fragment thereof.

In the case of single-chain Fv antibody fragments referred to hereinabove, the vector comprises one nucleic acid sequence encoding the VH and VL domains linked by a (poly)peptide linker, and in the case of Fab antibody fragments, the vector comprises two nucleic acid sequences encoding the VH-CH and the VL-CL chains.

In a further embodiment, the present invention relates to a host cell containing a nucleic acid sequence according to the present invention or a vector according to the present invention. The first (poly)peptide/protein of the present invention may be encoded by a nucleic acid sequence comprised on the same vector as the nucleic acid encoding the second (poly)peptide/protein of the present invention. In such case the host cell may comprise one vector comprising nucleic acid sequences encoding for both (poly)peptides/proteins. Alternatively, the first (poly)peptide/protein of the present invention may be encoded by a nucleic acid sequence comprised on a different vector as the nucleic acid encoding the second (poly)peptide/protein of the present invention. In that case, the host cell may comprise two different vector, one comprising a nucleic acid sequence encoding the first (poly)peptide/protein and one comprising a nucleic acid sequence encoding the second (poly)peptide/protein.

In the context of the present invention, the term "host cell" may be any of a number commonly used cells in the production of heterologous proteins, including but not limited to bacteria, such as *Escherichia coli* (Ge et al., 1995), or *Bacillus subtilis* (Wu et al., 1993), fungi, such as yeasts (Horwitz et al., 1988; Ridder et al., 1995) or filamentous fungus (Nyyssönen et al., 1993), plant cells (Hiatt & Ma, 1993; Whitelam et al., 1994), insect cells (Potter et al., 1993; Ward et al., 1995), or mammalian cells (Trill et al., 1995). In preferred embodiments, the host cell is a prokaryotic host cell, more preferable a Gram-negative host cell and most preferably *Escherichia coli*.

In a yet further preferred embodiment, the present invention relates to a modified variant of a wild type bacteriophage coat protein encoded by a nucleic acid sequence according to the present invention, a vector according to the present invention or produced by a host cell according to the present invention.

In another embodiment, the present invention relates to a bacteriophage particle displaying a (poly)peptide/protein on its surface obtainable by a method comprising:
  causing or allowing the attachment of said (poly)peptide/protein after expression to a member of the protein coat, wherein said attachment is caused by the formation of a disulphide bond between a first cysteine residue comprised in said member of the protein coat and a second cysteine residue comprised in said second (poly)peptide/protein, wherein said (poly)peptide/protein or said member of the protein coat comprises an amino acid with a pI greater than 8 which positively affects the reactivity of said first or said second cysteine residue. In certain embodiments said amino acid with a pI greater than 8 is comprised within said (poly)peptide/protein. In other embodiments, said amino acid with a pI greater than 8 is comprised within said member of the protein coat. In preferred embodiments said (poly)peptide/protein is a immunoglobulin, or a functional fragment thereof. In yet other embodiments, an amino acid with a pI greater than 8 is comprised in said first (poly)peptide/protein, preferably a member of the protein coat, and an amino acid with a pI greater than 8 is comprised in said second (poly)peptide/protein, preferably a immunoglobulin, or a functional fragment thereof In a highly preferred embodiment of the present invention, the bacteriophage particle contains a vector according to the present invention, wherein said vector comprises a first nucleic acid sequence comprising a first nucleic acid sequence encoding a first (poly)peptide/protein comprising a first cysteine residue and a second nucleic acid sequence comprising a second nucleic acid sequence encoding a second (poly)peptide/protein comprising a second cysteine residue, wherein one of said (poly)peptides/proteins comprises an amino acid with a pI greater than 8 which positively affects the reactivity of at least one of said cysteine residues. Most preferably, said second (poly)peptide/protein comprises at least a functional domain of an immunoglobulin.

The preferred embodiments of the method of the present invention referred to hereinabove mutatis mutandis apply to the bacteriophages of the present invention.

In a further embodiment, the present invention relates to a diverse collection of bacteriophage particles according to the present invention, wherein each of said bacteriophage particles displays a second (poly)peptide/protein out of a diverse collection of (poly)peptides/proteins.

A "diverse collection of bacteriophage particles" may as well be referred to as a "library" or a "plurality of bacteriophage particles". Each member of such a library displays a distinct member of the library.

In the context of the present invention, the term "diverse collection" refers to a collection of at least two particles or molecules which differ in at least part of their compositions, properties, and/or sequences. For example, a diverse collection of (poly)peptides/proteins is a set of (poly)peptides/proteins which differ in at least one amino acid position of their sequence. Such a diverse collection of (poly)peptides/proteins can be obtained in a variety of ways, for example by random mutagenesis of at least one codon of a nucleic acid sequence encoding a starting (poly)peptide/protein, by using error-prone PCR to amplify a nucleic acid sequence encoding a starting (poly)peptide/protein, or by using mutator strains as host cells in a method according to the present invention. These and additional or alternative methods for the generation of diverse collections of (poly)peptides/proteins are well-known to one of ordinary skill in the art. A "diverse collection of bacteriophage particles" may be referred to as a library or a plurality of bacteriophage particles. Each member of such a library displays a distinct member of the library.

In another embodiment, the invention relates to a method for obtaining a (poly)peptide/protein having a desired property comprising:

(a) providing the diverse collection of bacteriophage particles according to the present invention; and (b) screening said diverse collection and/or selecting from said diverse collection to obtain at least one bacteriophage particle displaying a (poly)peptide/protein having said desired property.

In the context of the present invention, the term "desired property" refers to a predetermined property which one of the (poly)peptides/proteins out of the diverse collection of (poly)peptides/proteins should have and which forms the basis for screening and/or selecting the diverse collection. Such desired properties comprise properties such as binding to a target, blocking of a target, activation of a target-mediated reaction, enzymatic activity, and further properties which are known to one of ordinary skill. Depending on the type of desired property, one of ordinary skill will be able to identify format and necessary steps for performing screening and/or selection. Most preferred is a method, wherein said desired property is binding to a target of interest.

Said target of interest can be presented to said diverse collection of bacteriophage particles in a variety of ways well known to one of ordinary skill, such as coated on surfaces for solid phase biopanning, linked to particles such as magnetic beads for biopanning in solution, or displayed on the surface of cells for whole cell biopanning or biopanning on tissue sections. Bacteriophage particles having bound to said target can be recovered by a variety of methods well known to one of ordinary skill, such as by elution with appropriate buffers, either by using a pH- or salt gradient, or by specific elution using soluble target.

In a preferred embodiment, the method for obtaining a (poly)peptide/protein further comprises:

(ba) contacting said diverse collection of bacteriophage particles with the target of interest;

(bb) eluting bacteriophage particles not binding to the target of interest;

(bc) eluting bacteriophage particles binding to the target of interest by treating the complexes of target of interest and bacteriophages binding to said target of interest formed in step (ba) under reducing conditions.

Under reducing conditions, such as by incubation with DTT, the disulfide bonds are cleaved, thus allowing to recover the specific bacteriophage particles for further rounds of biopanning and/or for identification of the (poly)peptide/proteins specifically binding to said target.

In other embodiments, the invention relates to a method to improve a cysteine display system by introducing an amino acid with a pI greater than 8 into a first or a second (poly)peptide/, such that a first cysteine residue comprised in said first (poly)peptide/protein more preferably forms a disulphide bond with a second cysteine residue comprised in a second (poly)peptide/protein than in an equivalent cysteine display system into which no such amino acid with a pI greater than 8 has been introduced.

In other embodiments, the invention relates to a complex comprising (a) a first (poly)peptide/protein comprising a first cysteine residue, and (b) a second (poly)peptide/protein comprising a second cysteine residue, wherein one of said (poly)peptides/proteins further comprises an amino acid with a pI greater than 8 which positively effects the reactivity of at least one of said cysteines residues, and wherein said first and said second (poly)peptide/protein form a disulphide bond via said cysteine residues. In preferred embodiments, said second (poly)peptide/protein is a member of a diverse collection of second (poly)peptides/proteins displayed on a diverse collection of a plurality of bacteriophage particles. In certain preferred embodiments said first (poly)peptide/protein is a phage coat protein. In other preferred embodiments, said second (poly)peptides/protein comprises an immunoglobulin or a functional fragment thereof, more preferably a scFv or Fab fragment. In other embodiments, the present invention provides a host cell comprising any of the complexes described hereinabove.

EXAMPLES

Example 1

Construction of Novel Vectors

Vectors are based on known expression vectors described in WO 01/05909. Heavy and light chains of Fab fragments are expressed from a dicistronic phagemid under the control of the lac promotor/operator region. The first expression cassette comprises the signal sequence ompA and the variable and constant domain of the light chain. The second expression cassette comprises the signal sequence phoA and the variable and constant domain of the heavy chain. Heavy and light chain are not linked via a disulfide bond. Gene III is also encoded on the same vector. The cysteine residues forming the disulphide bond are located at the N-terminus of pIII and at the C-terminus of the heavy chain Fd-fragment. The main features of a typical CysDisplay vector are shown in FIG. 1.

New display vector variants (pMORPH25 versions A, B, C and E) have been constructed based on the pMORPH25 vector, which is a derivative of pMORPH23 (described in WO 04/013276). The sequence and the vector maps of pMORPH23 and pMORPH25 containing an Estrodiol-BSA specific HuCAL Fab fragment are shown in FIGS. 5 (SEQ ID NO: 21), 6, 7 (SEQ ID NO: 22) and 8. The Cystein-Tag sequences of pMORPH23 and pMORPH25 are identical.

For construction of vector variants with a modified Cystein-Tag, pMORPH25 has been digested by EcoRI and HindIII to remove the C-terminal wild-type sequence (pMORPH25_WT tag). New C-terminal tags of version A, B, C and E were inserted by ligation of annealed double stranded (ds) oligonucleotides with compatible overhangs to EcoRI and HindIII digested display vector pMORPH25.

The sequence of the respective oligonucleotides are summarized in Table 2. Double stranded oligonucleotide were annealed according to the following procedure. 200 ng each of the respective oligonucleotide combination (e.g. Seq ID No1 and Seq ID No2 for pMORPH25 version A) were incubated for 20 min at 99° C. followed by cooling down to room temperature, allowing annealing of complementary sequences. Annealed dsDNA was ligated into digested pMORPH25 according to standard DNA techniques (see, e.g., Sambrook et al., 2001; Ausubel et al., 1999; Kay et al., 1996) and transformed into electro-competent Top10F cells (Invitrogen).

TABLE 2

Oligonucleotides used for display tag cassette construction

Seq ID No 1:
pMORPH25_A_for
5'aattcccaggggggagcggaggtgcgccgcaccatcatcaccatca
ctgcaaatgata3'

Seq ID No 2:
pMORPH25_A_rev
5'agcttatcatttgcagtgatggtgatgatggtgcggcgcacctccg
ctcccccctggg3'

Seq ID No 3
pMORPH25_B_for
5'aattcccaggggggagcggaggtgcgccgcaccatcataaacatca
ctgctgata3'

TABLE 2-continued

Oligonucleotides used for display tag cassette construction

Seq ID No 4
pMORPH25_B_rev
5'agcttatcagcagtgatgtttatgatggtgcggcgcacctccgctc
ccccctggg3'

Seq ID No 5
pMORPH25_C_for
5'aattcccaggggggagcggaggtgcgccgcaccatcatcaccataa
atgctgata3'

Seq ID No 6
pMORPH25_C_rev
5'agcttatcagcatttatggtgatgatggtgcggcgcacctccgctc
ccccctggg3'

Seq ID No 7
pMORPH25_E_for
5'aattcccaggggggagcggaggtgcgccgcacaaacataaacataa
atgctgata3'

Seq ID No 8
pMORPH25_E_rev
5'agcttatcagcatttatgtttatgtttgtgcggcgcacctccgctc
ccccctggg3'

The amino acid sequence of the C-terminus of the heavy chain fragment of the control construct pMORPH25 is shown in Table 3. Four such derivatives are labelled as "pMORPH25 version A", "pMORPH25 version B", "pMORPH25 version C" and "pMORPH25 version E" in Table 3. One variant carries an extra lysine residue at the very C-terminus (variant A). In variants B and C, a histidine residue, three and one amino acids N-terminal to the reactive cysteine residue, respectively, was exchanged to a lysine residue. In variant E three out of the five histidine residues directly N-terminal to the reactive cysteine residue were exchanged to lysine residues.

TABLE 3

Amino acid sequences of the C-termini of the heavy chain fragment used in the present invention

| Construct | C-terminus of the heavy chain fragment |
| --- | --- |
| pMORPH25 | PGGSGGAPHHHHHHC |
| pMORPH25 version A | PGGSGGAPHHHHHHCK |
| pMORPH25 version B | PGGSGGAPHHHKHHC |
| pMORPH25 version C | PGGSGGAPHHHHHKC |
| pMORPH25 version E | PGGSGGAPHKHKHKC |

Example 2

Phage Binding to Ni-NTA Plates

The six histidine residues directly N-terminal to the reactive cysteine residue in pMORPH25 confer the bacteriophage particles with the capability to bind to Ni-NTA plates. In version A a lysine residue was introduced C-terminal to the reactive cysteine residue. In versions B, C and E of pMORPH25 this stretch of six histidine residues was destroyed by way of introduction of at least one lysine residue into each of said hexa-histidine stretches. Presumably, this should lead to a loss of the capability of the bacteriophage particles displaying the Fab fragments to bind to Ni-NTA plates.

Bacteriophage particles displaying Fab fragments were produced via standard techniques (see e.g. Kay et al, 1996 and Example 2.2 of WO 01/05909). Binding of bacteriophage particles to Ni-NTA plates was determined as briefly outlined. Phage particle ($8\times10^8$/well), which were pre-incubated for 2 hours with blocking solution (Chemiblock diluted with TBS, 0.1% Tween20), were added to pre-blocked HIS-select iLAP HC nickel coated 96 well plates (Sigma-Aldrich Co). After washing with PBST and PBS, remaining phages were visualized with an anti-M13-HRP conjugate (Amersham Pharmacia Biotech) and BM blue soluble (Boehringer Mannheim). Results are depicted in FIG. 2.

As can be seen in FIG. 2, versions B and E of pMORPH25 effectively destroyed the histidine tag. The original construct still bound to Ni-NTA plates. The same holds true for version A, which still carries the hexa-histidine tag, as well as for version C, which still carries a penta-histidine tag, which seems to be sufficient to enable binding of the bacteriophage particles to the Ni-NTA plates.

Example 3

Relative Display Rate

The relative display rate of phage particles of the various vector constructs (version A-version E, as outlined in Example 1) were determined as described below.

Phage particles were produced by standard procedure (see e.g. Kay et al, 1996 and Example 2.2 of WO 01/05909). The phage particle number and the antibody display rate of an unknown phage particle solution was determined in two independent ELISA experiments.

The Phage particle titer of a phage preparation is determined via an anti-pIII capture ELISA, and the antibody display rate of a phage preparation was determined via an anti-Fd capture ELISA. The relative display rate is defined as the anti-Fd signal divided by the anti-pIII capture ELISA signal.

Maxisorp Nunc-Immuno microtiter plates were coated with 100 µl of a 2.5 µg/ml anti-pIII capture antibody solution (MoBiTech, Göttingen, Germany) and a second plate with 100 µl of 0.5 µg/ml anti-Fd capture antibody solution for 12 hours at 4° C. and blocked for 2 h at room temperature with Chemiblock solution (Chemichon, International) diluted 1:2 in TPBS. Serial dilutions of phage particles were added to the plates for 2 hours. After five times washing with TBST, captured phage particles were detected via an anti-M13-HRP antibody (anti-g8p specific, Amersham) followed by fluorescence detection (QuantaBlue, Pierce).

Phage particle titers can be calculated from a calibration curve of a reference phage solution with known particle concentration. The display rate was calculated from a defined reference phage particle preparation with a known antibody fragment display rate. The display rate of this reference phage preparation has been determined according to Johansen, L. K. et al. (1995).

The relative display rates are summarized in Table 4. The display rate with the original pMORPH25 construct was set to 100 percent.

TABLE 4

Relative display rates of the constructs of this study

|  | Experiment #1 | Experiment #2 | Experiment #3 |
|---|---|---|---|
| pMORPH25 | 1.00 | 1.00 | 1.00 |
| pMORPH25 version A | 0.98 | 1.52 |  |

TABLE 4-continued

Relative display rates of the constructs of this study

|  | Experiment #1 | Experiment #2 | Experiment #3 |
|---|---|---|---|
| pMORPH25 version B | 1.29 | 2.14 | 1.51 |
| pMORPH25 version C | 1.25 | 1.67 |  |
| pMORPH25 version E |  |  | 2.57 |

As can be seen, all four derivatives of pMORPH25 showed higher relative display rates as compared to pMORPH25 itself. The highest display rate showed pMORPH25 version E, which exhibited a 2.57-fold increased display rate over the original construct pMORPH25.

This experiment shows the surprising result that the destruction of the hexa-histidine tag, achieved via the introduction of the positively charged amino acid lysine, leads to an increased display rate on the bacteriophage particles.

Example 4

Functional Display Rate

The functional display rates were measured in an antigen binding ELISA assay, which is specific for the particular binder used in this study.

1 µg recombinant protein was coated onto Maxisorp Nunc-Immuno microtiter plates for 12 hours at 4° C. and blocked with PBS containing 5% skimmed milk powder (J. M. Gabler Saliter GmbH & Co KG) for 2 h at room temperature. Phage preparations from the various tag constructs were pre-incubated in PBS, 5% skimmed milk powder and 0.05% Tween 20 in the presence or absence of 20 mM DTT. Serial dilutions of pre-blocked bacteriophage particles were added to the coated Maxisorp wells and incubated for 2 hour. After washing with PBST and PBS, remaining phages were visualized with an anti-M13-HRP conjugate (Amersham Pharmacia Biotech) and BM blue soluble (Boehringer Mannheim).

In a first set of control experiments additionally 25 mM DTT were added to the wells. In a second set of control experiments plates were coated with BSA only. Results are shown in FIG. 3 for the pMORPH25 versions A, B and C and in FIG. 4 for pMORPH25 versions E.

Functional bacteriophage particles were identified for all constructs tested. pMORPH25 version A is slightly better than the pMORPH25 standard. Versions B and C of pMORPH25 are clearly better than the pMORPH25 standard. Most pronounced are the differences when the individual wells are inoculated with at least 5e+08 bacteriophage particles per well. The functional display rate of pMORPH25 version E is even about 4-times higher than the display rate of the pMORPH25 standard (indicated by the arrows in FIG. 4). All control measurement, i.e. wells into which additionally 25 mM DTT was added and wells in plates coated with BSA, didn't give signals above background.

This experiment shows the surprising result that the destruction of the hexa-histidine tag, achieved via the introduction of the positively charged amino acid lysine, not only leads to an increased display rate on the bacteriophage particles, but that the increased display rate goes hand in hand with functional binding of bacteriophage particles. In fact, the increase of the functional display rate is even higher than the increase of the relative display rate measured in the foregoing experiment.

Example 5

Display of Diverse Libraries

This example shows that improvements in the display rate by modified tag versions (see Table 4) is not restricted to a specific Fab fragment, but can generically applied to a diverse Fab fragment library. The relative display rates of a Fab library containing heavy chain fragments of pMORPH25 version E (C-terminus: -HKHKHKC) were compared to a Fab library containing heavy chain fragments of the original pMORPH23 vector (C-terminus: -HHHHHHC). See Table 3 for a comparison (the Cysteine-Tag sequences of pMORPH23 and pMORPH25 are identical). The experimental set up was identical as described in Example 3. Results are illustrated in FIG. 9.

As can be seen, essentially all frameworks comprising polypeptides according to the present invention show a clearly improved display rate as compared to conventional vectors (set to 1). Furthermore, the increased relative display rate is observed with both, lambda and kappa chain fragments.

BRIEF DESCRIPTION OF THE DRAWINGS

FIG. 1: A Typical CysDisplay Vector

Heavy chains and light chains of Fab fragments are under control of the lac promotor/operator region. The first expression cassette comprises the signal sequence ompA and the variable (VL) and constant domain (CL) of the light chain, the second expression cassette comprises the signal sequence phoA and the variable (VH) and constant domain (CH1) of the heavy chain. Heavy and light chain are not linked via a disulfide bond. Gene III is also encoded on the same vector (gIII). The cysteines forming the disulphide bond are located at the N-terminus of pIII and at the C-terminus of the heavy chain Fd-fragment (indicated by a 'C'). AccI, AflII, XbaI, EcoRI and HindIII indicate restriction sites which may be conveniently used to generate or modify the display vector.

FIG. 2: Binding to Ni-NTA Plates

"pM25" stands for the original "pMORPH25" construct, and "pM25_A" through "pM25_E" stand for the constructs "pMORPH25 version A" through "pMORPH25 version E", respectively. "pM25 w/o HIS tag" stands for a construct in which the histidine tag was deleted. Absorbance was measured at 370 nm.

FIG. 3: Functional Display Rates of pMORPH Versions A, B and C

"pM25" stands for the original "pMORPH25" construct, and "pM25_A" through "pM25_E" stand for the constructs "pMORPH25 version A" through "pMORPH25 version E", respectively. The bars from left to right for each construct are as follows: 5.0e+10 bacteriophage particles per well, 5.0e+9 bacteriophage particles per well, 5.0e+8 bacteriophage particles per well, 5.0e+7 bacteriophage particles per well, 5.0e+10 bacteriophage particles per well plus 25 mM DTT, and 5.0e+10 bacteriophage particles per well in a plate coated with BSA.

FIG. 4: Functional Display Rate of pMORPH Version E

"pM25" stands for the original "pMorph25" construct, and "pM25_E" stands for the construct "pMORPH25 version E". The bars from left to right for each construct are as follows: 1.0e+10 bacteriophage particles per well, 1.0e+9 bacteriophage particles per well, 5.0e+8 bacteriophage particles per well, 2.5e+8 bacteriophage particles per well, 1.25e+8 bacteriophage particles per well, 6.25e+7 bacteriophage particles per well, 1.0e+10 bacteriophage particles per well in a plate coated with BSA, and 1.0e+10 bacteriophage particles per well plus 25 mM DTT. The arrows indicates those measurements, in which the difference between the pMORPH25 standard and pMORPH25 version E was most pronounced.

FIGS. 5 A-B shows the sequence of a pMORPH23-derivative containing an Estrodiol-BSA specific HuCAL Fab fragment FIG. 6: shows a vector map of a pMORPH23-derivative containing an Estrodiol-BSA specific HuCAL Fab fragment FIGS. 7 A-B shows the sequence of a pMORPH23-derivative containing an Estrodiol-BSA specific HuCAL Fab fragment FIG. 8 shows a vector map of a pMORPH25-derivative containing an Estrodiol-BSA specific HuCAL Fab fragment FIG. 9 shows the relative display rate of Fab fragment libraries based on the present invention compared to libraries of conventional constructs. The display rates of the conventional constructs (pMORPH23) were set to 1 (i.e. 100%) for each individual construct. Shown are the relative display rates of the improved constructs, exemplified by pMORPH25-version E, in relation to the display rate of the pMORPH23 constructs. The different frameworks tested are indicated on the x-axis. The white bars indicate lambda chain fragments, the black bar indicate kappa chain fragments.

REFERENCES

Albrecht, H., DeNardo, G. L. & DeNardo, S. J. (2006) Monospecific bivalent scFv-SH: Effects of linker length and location of an engineered cysteine on production, antigen binding activity and free SH accessibility. Journal of Immunological Methods, 310, 100-116.

Ausubel, F. M., Brent, R., Kingston, R. E., Moore, D. D., Sedman, J. G., Smith, J. A. & Struhl, K. eds. (1999). Current Protocols in Molecular Biology. New York: John Wiley and Sons.

Bass, S., Greene, R. & Wells, J. A. (1990) Hormone phage: an enrichment method for variant proteins with altered binding properties. Proteins: Structure, Function and Genetics 8, 309-314.

Bird, R. E., Hardman, K. D., Jacobson, J. W., Johnson, S., Kaufman, B. M., Lee S. M., Lee T., Pope S. H., Riordan G. S. & Whitlow M. (1988). Single-chain antigen-binding proteins [published erratum appears in (1989). Science 244, 409]. Science 242, 423-6.

Brinkmann, U., Reiter, Y., Jung, S., Lee, B. & Pastan, I. (1993). A recombinant immunotoxin containing a disulfide-stabilized Fv fragment. Proc. Natl. Acad. Sci. U.S.A. 90, 7538-7542.

Britto, P. J., Knipling, L. & Wolff, J. (2002) The Local Electrostatic Environment Determines Cysteine Reactivity in Tubulin. Journal of Biological Chemistry, 2002, 29018-29027.

Bulja, G., Kortemme, T. & Goldenberg, D. P. (1998) Ionization-Reactivity Relationships for Cysteine Thiols in Polypeptides. Biochemistry 37, 8965-8972.

Crameri, R., & Suter, M. (1993). Display of biologically active proteins on the surface of filamentous phages: a cDNA cloning system for selection of functional gene products linked to the genetic information responsible for their production. Gene 137, 69-75.

Crissman, J. W. & Smith, G. P. (1984). Gene-III protein of filamentous phages: evidence for a carboxy-terminal domain with a role in morphogenesis. Virology 132, 445-455.

Dunn, I. S. 1996. Phage display of proteins. Curr. Opin. Biotechnol. 7:547-553.

Gao, C., Mao, S., Lo, C.-H. L., Wirsching, P., Lerner, R. A., & Janda, K. D. (1999). Making artificial antibodies: A format for phage display of combinatorial heterodimeric arrays. Proc. Natl. Acad. Sci. U.S.A. 96, 6025-6030.

Ge, L., Knappik, A., Pack, P., Freund, C. & Plückthun, A. (1995). Expressing antibodies in *Escherichia coli*. Antibody Engineering. A Practical Approach (Ed. C.A.K. Borrebaeck). IRL Press, Oxford, pp. 229-266.

Glockshuber, R., Malia, M., Pfitzinger, I. & Plückthun, A. (1992). A comparison of strategies to stabilize immunoglobulin Fv-fragments. Biochemistry 29, 1362-1366.

Greenwood J., Willis A. E. & Perham R. N. (1991) Multiple display of foreign peptides on a filamentous bacteriophage. Peptides from *Plasmodium falciparum* circumsporozoite protein as antigens. J. Mol. Biol. 220, 821-827.

Hansen, R. E:, Ostergaard, H. & Winther, J. R. (2005) Increasing the Reactivity of an Artificial Dithiol-Disulfide Pair through Modification of the Electrostatic Milieu. Biochemistry, 44, 5899-5906-

Hiatt, A. & Ma, J. K. (1993). Characterization and applications of antibodies produced in plants. Int. Rev. Immunol. 10, 139-152.

Hochuli, E., Bannwarth, W., Döbeli, H., Gentz, R. & Stüber, D. (1988). Genetic approach to facilitate purification of recombinant proteins with a novel metal chelate adsorbent. Bio/Technology 6, 1321-1325.

Hopp, T. P., Prickett, K. S., Price, V. L., Libby, R. T., March, C. J., Cerretti, D. P., Urdal, D. L. & Conlon, P. J. (1988). A short polypeptide marker sequence useful for recombinant protein identification and purification. Bio/Technology 6, 1204-1210.

Horwitz, A. H., Chang, C. P., Better, M., Hellstrom, K. E. & Robinson, R. R. (1988). Secretion of functional antibody and Fab fragment from yeast cells. Proc. Natl. Acad. Sci. U.S.A. 85, 8678-8682.

Huston, J. S., Levinson, D., Mudgett-Hunter, M., Tai, M. S., Novotny, J., Margolies, M. N., Ridge, R. J., Bruccoleri, R. E., Haber, E. & Crea, R. (1988). Protein engineering of antibody binding sites. Recovery of specific activity in an anti-digoxin single-chain Fv analogue produced in *Escherichia coli*. Proc. Natl. Acad. Sci. U.S.A. 85, 5879-5883.

Jespers L. S., Messens J. H., De Keyser A., Eeckhout D., Van d. B., I, Gansemans Y. G., Lauwereys M. J., Vlasuk G. P. & Stanssens P. E. (1995). Surface expression and ligand-based selection of cDNAs fused to filamentous phage gene VI. Biotechnology (N.Y.) 13, 378-382.

Kay, B. K., Winter, J. & McCafferty, J., eds. (1996). Phage display of peptides and proteins: a laboratory manual. Academic Press, Inc., San Diego.

Knappik, A. & Plückthun, A. (1994). An improved affinity tag based on the FLAG peptide for detection and purification of recombinant antibody fragments. BioTechniques 17, 754-761.

Knappik, A., Ge, L., Honegger, A., Pack, P., Fischer, M., Wellnhofer, G., Hoess, A., Wölle, J., Plückthun, A. & Virnekäs, B. (2000). Fully synthetic Human Combinatorial Antibody Libraries (HuCAL) based on modular consensus frameworks and CDRs randomized with trinucleotides. J. Mol. Biol. 296, 57-86.

Krebber, C. (1996). Selektiv infektiöse Phagen: In vivo Selektion auf Interaktionen zwischen Protein and Ligand. Dissertation at the University of Zurich.

Krebber, C., Spada, S., Desplancq, D., Krebber, A., Ge, L. & Plückthun, A. (1997). Selectively-infective phage (SIP): A mechanistic dissection of a novel in vivo selection for protein-ligand interactions. J. Mol. Biol. 268, 607-618.

Lindner, P., Guth, B., Wülfing, C., Krebber, C., Steipe, B., Müller, F. & Plückthun, A. (1992). Purification of native proteins from the cytoplasm and periplasm of *Escherichia coli* using IMAC and histidine tails: a comparison of protocols and protocols. Methods: A Companion to Methods Enzymol. 4, 41-56.

Maruyama I. N., Maruyama H. I. & Brenner S. (1994) Lambda foo: a lambda phage vector for the expression of foreign proteins. Proc. Natl. Acad. Sci. U.S.A. 91, 8273-8277.

McGregor, D. (1996). Selection of proteins and peptides from libraries displayed on filamentous bacteriophage. Mol. Biotechnol. 6:155-162.

Mikawa Y. G., Maruyama I. N. & Brenner S. (1996). Surface display of proteins on bacteriophage lambda heads. J. Mol. Biol. 262, 21-30.

Nyyssönen, E., Penttila, M., Harkki, A., Saloheimo, A., Knowles, J. K. & Keranen, S. (1993). Efficient production of antibody fragments by the filamentous fungus *Trichoderma reesei*. Bio/Technology 11, 591-595.

Parmley S. F. & Smith G. P. (1988) Antibody-selectable filamentous fd phage vectors: affinity purification of target genes. Gene 73, 305-318.

Potter, K. N., Li, Y. & Capra, J. D. (1993). Antibody production in the baculovirus expression system. Int. Rev. Immunol. 10, 103-112.

Ridder, R., Schmitz, R., Legay, F. & Gram, H. (1995). Generation of rabbit monoclonal antibody fragments from a combinatorial phage display library and their production in the yeast *Pichia pastoris*. Bio/Technology 13, 255-260.

Sambrook, J, & Russell, D. (2001). Molecular Cloning: A laboratory manual (Third edition), Cold Spring Harbor Laboratory Press, Cold Spring Harbor, USA.

Schmidt, T. G. & Skerra, A. (1994). One-step affinity purification of bacterially produced proteins by means of the "Strep tag" and immobilized recombinant core streptavidin. J. Chromatogr. A 676, 337-345.

Schmidt, T. G., Koepke, J., Frank, R., Skerra, A. (1996). Molecular interaction between the Strep-tag affinity peptide and its cognate target, streptavidin. J. Mol. Biol. 255, 753-766.

Skerra, A. & Plückthun, A. (1988). Assembly of a functional immunoglobulin Fv fragment in *Escherichia coli*. Science 240, 1038-1041.

Smith G. P. (1985). Filamentous fusion phage: novel expression vectors that display cloned antigens on the virion surface. Science 228, 1315-1317.

Snyder, G. H., Cennerazzo, M. J., Karalis, A. J. & Filed, D. (1981). Electrostatic Influence of Local Cysteine Environments on Disulfide Exchange Kinetics. Biochemistry 20, 6509-6519.

Snyder, G. H., Reddy, M. K., Cennerazzo, M. J. & Filed, D. (1983). Use of local electrostatic environments of cysteines to enhance formation of a desired species in a reversible disulfide exchange reaction. Biochimica et Biophysica Acta 749, 219-226.

Sternberg N. & Hoess R. H. (1995). Display of peptides and proteins on the surface of bacteriophage lambda. Proc. Natl. Acad. Sci. U.S.A. 92, 1609-1613.

Trill, J. J., Shatzman, A. R. & Ganguly, S. (1995). Production of monoclonal antibodies in COS and CHO cells. Curr. Opin. Biotechnol. 6, 553-560.

Ward, V. K., Kreissig, S. B., Hammock, B. D. & Choudary, P. V. (1995). Generation of an expression library in the baculovirus expression vector system. J. Virol. Methods 53, 263-272.

Whitelam, G. C., Cockburn, W. & Owen, M. R. (1994). Antibody production in transgenic plants. Biochem. Soc. Trans. 22, 940-944.

Wu, X. C., Ng, S. C., Near, R. I. & Wong, S. L. (1993). Efficient production of a functional single-chain anti-digoxin antibody via an engineered *Bacillus subtilis* expression-secretion system. Bio/Technology 11, 71-76.

The invention claimed is:

1. A method for increasing the display rates of an antibody fragment on the surface of bacteriophage particle, comprising
   (a) artificially introducing a first cysteine residue within ten amino acids of the N-terminus of a coat protein of a bacteriophage and artificially introducing a second cysteine residue within fifteen amino acids of the C-terminus of the antibody fragment,
   (b) artificially introducing lysine or arginine amino acid within five amino acids of the artificially introduced first and/or second cysteine residue of step (a),
   wherein said lysine or arginine amino acid positively affects the reactivity of at least one of said artificially introduced cysteine residues,
   (c) causing or allowing the attachment of the coat protein to the antibody fragment,
   wherein said attachment is caused by the formation of a disulphide bond between the first cysteine residue comprised in said coat protein and the second cysteine residue comprised in said antibody fragment.

2. The method of claim 1, wherein said coat protein of a bacteriophage and said antibody fragment are expressed and assembled in an appropriate host cell.

3. The method of claim 1, wherein said disulphide bond is formed in the periplasmatic space of a host cell.

4. The method of claim 1, wherein said disulphide bond is a intermolecular disulphide bond.

5. The method of claim 1, wherein said amino acid of step (b) is lysine.

6. The method of claim 1, wherein said protein coat comprises a truncated variant of a wild type coat protein of a bacteriophage, wherein said truncated variant comprises at least that part of said wild type coat protein causing the incorporation of said coat protein into the protein coat of the bacteriophage particle.

7. The method of claim wherein said protein coat comprises a variant of a wild type coat protein of a bacteriophage, wherein said variant is capable of being incorporated into the protein coat of the bacteriophage particle.

8. The method of claim 6, wherein said first cysteine residue has been artificially introduced into said truncated variant of a wild type coat protein of a bacteriophage.

9. The method of claim 7, wherein said first cysteine residue has been artificially introduced into a variant of a wild type coat protein of a bacteriophage.

10. The method of claim 1, wherein said bacteriophage particle is a bacteriophage particle of a filamentous bacteriophage.

11. The method of claim 1, wherein said protein coat of a bacteriophage particle is or is derived from the wild type coat protein pIII.

12. The method of claim 1, Wherein said protein coat of the bacteriophage particle is or is derived from the wild type coat protein pIX.

13. The method of claim 1, wherein said antibody fragment is a scFv or Fab fragment.

* * * * *

UNITED STATES PATENT AND TRADEMARK OFFICE
CERTIFICATE OF CORRECTION

PATENT NO. : 9,062,097 B2  
APPLICATION NO. : 12/664533  
DATED : June 23, 2015  
INVENTOR(S) : Prassler et al.

Page 1 of 1

It is certified that error appears in the above-identified patent and that said Letters Patent is hereby corrected as shown below:

In the Claims

| Claim | Line | PTO | Should be |
|---|---|---|---|
| 1 | 8 | "artificially introducing lysine" | artificially introducing --a-- lysine |
| 7 | 1 | "The method of claim wherein" | The method of claim --1,-- wherein |
| 12 | 1 | "The method of claim 1, Wherein said" | The method of claim 1, --wherein-- said |

Signed and Sealed this  
Twenty-fourth Day of November, 2015

Michelle K. Lee  
*Director of the United States Patent and Trademark Office*